(12) United States Patent
Bhatt

(10) Patent No.: US 11,446,243 B1
(45) Date of Patent: Sep. 20, 2022

(54) ORAL LIQUID COMPOSITIONS INCLUDING VALSARTAN

(71) Applicant: ECI Pharmaceuticals, LLC, Fort Lauderdale, FL (US)

(72) Inventor: Nirali R. Bhatt, North Lauderdale, FL (US)

(73) Assignee: ECI PHARMACEUTICALS, LLC, Fort Lauderdale, FL (US)

( * ) Notice: Subject to any disclaimer, the term of this patent is extended or adjusted under 35 U.S.C. 154(b) by 0 days.

(21) Appl. No.: 16/920,532

(22) Filed: Jul. 3, 2020

Related U.S. Application Data

(60) Provisional application No. 62/882,947, filed on Aug. 5, 2019.

(51) Int. Cl.
| | |
|---|---|
| *A61K 45/06* | (2006.01) |
| *A61K 9/00* | (2006.01) |
| *A61P 3/06* | (2006.01) |
| *A61K 47/40* | (2006.01) |
| *A61K 9/08* | (2006.01) |
| *A61K 31/41* | (2006.01) |

(52) U.S. Cl.
CPC ............ *A61K 9/0053* (2013.01); *A61K 9/08* (2013.01); *A61K 31/41* (2013.01); *A61K 47/40* (2013.01)

(58) Field of Classification Search
CPC ............... A61K 9/0053; A61K 31/724; A61K 2300/00; A61K 45/06; A61K 47/40; A61K 9/10; A61K 9/08; A61K 47/6951; A61K 8/738; A61K 2800/49; A61K 8/04; A61P 9/00; A61P 9/12; A61P 9/10; A61P 9/14; A61P 35/00
See application file for complete search history.

(56) References Cited

U.S. PATENT DOCUMENTS

| | | |
|---|---|---|
| 5,399,578 A | 3/1995 | Buhlmayer et al. |
| 10,478,422 B1 | 11/2019 | Thomas |
| 10,548,838 B1 | 2/2020 | Thomas |
| 2007/0026026 A1 * | 2/2007 | Delmarre ............ A61K 9/0095 424/400 |
| 2007/0093542 A1 | 4/2007 | Rukhman et al. |
| 2008/0152717 A1 * | 6/2008 | Doney ................. A61K 31/41 424/489 |
| 2008/0274196 A1 * | 11/2008 | Jayanthi .............. A61K 9/1623 424/489 |
| 2010/0222334 A1 | 9/2010 | Talamonti |
| 2010/0267787 A1 | 10/2010 | Harasymiw et al. |
| 2011/0196026 A1 * | 8/2011 | De ......................... A61K 9/19 514/449 |
| 2013/0102594 A1 | 4/2013 | Talamonti et al. |
| 2013/0109729 A1 | 4/2013 | Talamonti et al. |
| 2014/0011854 A1 * | 1/2014 | Tyavanagimatt ....... A61P 31/20 514/410 |
| 2017/0224834 A1 * | 8/2017 | Leighton .............. A61K 47/64 |
| 2020/0276161 A1 | 9/2020 | Thomas |

FOREIGN PATENT DOCUMENTS

| | | | | |
|---|---|---|---|---|
| EP | 2735305 A1 * | 5/2014 | ........ | A61K 9/0019 |
| WO | WO-2005056607 A1 * | 6/2005 | ........ | B82Y 5/00 |
| WO | WO 2009/064681 A2 | 5/2009 | | |

OTHER PUBLICATIONS

Black, Henry R., et al. "Valsartan: more than a decade of experience." Drugs, vol. 69, No. 17, 2009, p. 2393+. Gale Academic OneFile, Accessed Aug. 6, 2020. (Year: 2009).*
Diovan, Feb. 19, 2017, 19 pages.
Prexxartan, Dec. 19, 2017, 23 pages.
U.S. Appl. No. 16/715,294, filed Dec. 16, 2019.

* cited by examiner

*Primary Examiner* — Tracy Liu

(74) *Attorney, Agent, or Firm* — K&L Gates LLP

(57) ABSTRACT

The present disclosure provides an oral liquid composition comprising valsartan with enhanced solubility and stability. Also, provided herein are methods of using the oral liquid compositions for the treatment of hypertension, treatment of heart failure and reduction of cardiovascular mortality in clinically stable patients with left ventricular failure or left ventricular dysfunction following myocardial infarction.

42 Claims, 7 Drawing Sheets

SECTION "A" - "A"

ORAL LIQUID COMPOSITIONS INCLUDING VALSARTAN

CROSS-REFERENCE TO RELATED APPLICATIONS

The present application claims priority under 35 U.S.C. 119(e) to U.S. Provisional Patent Application Ser. No. 62/882,947, filed Aug. 5, 2019, the entire disclosure of which is hereby incorporated herein by reference.

FIELD OF THE INVENTION

Provided herein are oral liquid compositions including valsartan with enhanced solubility. Also provided herein, are methods of using oral liquid compositions including valsartan for the treatment of hypertension, treatment of heart failure, and reduction of cardiovascular mortality in clinically stable patients with left ventricular failure or left ventricular dysfunction following myocardial infarction.

BACKGROUND

Valsartan is a nonpeptide, orally active, and specific angiotensin II receptor blocker acting on the $AT_1$ receptor subtype. Angiotensin II interacts with specific receptors on the surface of a target cell. It has been possible to identify receptor subtypes which are termed, e.g., $AT_1$- and $AT_2$-receptors. Significant efforts have been made to identify substances that bind to the $AT_1$-receptor. Such active ingredients are often termed angiotensin II antagonists. Because of the inhibition of the $AT_1$-receptor, such antagonists can be used, e.g., as antihypertensives or for the treatment of congestive heart failure. Angiotensin II antagonists are therefore understood to be those active ingredients which bind to the $AT_1$-receptor subtype. Prolonged and uncontrolled hypertensive vascular disease ultimately leads to a variety of pathological changes in target organs such as the heart and kidney. Sustained hypertension can lead an increased occurrence of stroke.

Valsartan is chemically described as N-(1-oxopentyl)-N-[[2'-(1H-tetrazol-5-yl)[1,1'-biphenyl]-4-yl]methyl]-L-valine. Valsartan is used for treating hypertension, treatment of heart failure, and reduction of cardiovascular mortality in clinically stable patients with left ventricular failure or left ventricular dysfunction following myocardial infarction.

Valsartan is typically administered as a solid oral dosage form such as, for example, tablets, pills, and capsules. Oral ingestion is the most convenient and commonly employed route of drug delivery due to its ease of administration, high patient compliance, cost effectiveness, reduced sterility constraints, and flexibility in the design of dosage form.

However, some patients, specifically pediatric and geriatric patient populations, may dislike or have difficulty swallowing solid oral dosage forms, which can lead to associated disadvantages, such as patient non-compliance. In such situations, oral liquid dosage forms, including solutions, suspensions, and emulsions, can be easier to administer and more suitable for use.

Many marketed pharmaceutical products do not have regulatory approval for pediatric use, resulting in "off-label" prescribing by physicians. When a pharmaceutical product does not have a labeled indication for children, manufacturers do not produce strengths and dosage forms appropriate for the pediatric population. Extemporaneously-prepared formulations are a sub-optimal option in instances where commercial liquid formulations are not available. At present, liquid dosage forms for valsartan are prepared by compounding tablets into a suspension. However, developing and compounding of pediatric formulations can be challenging for dispensing pharmacists, resulting in a variety of issues, including inaccurate dosing, poor stability, poor taste, adherence problems, and lack of standardizations in extemporaneous compounding. Consumers requiring a liquid dosage form may be putting themselves at risk since the product may not be made consistently from one pharmacist to another. Further, extemporaneously-prepared valsartan formulations have a short shelf life, typically a maximum shelf life of only 90 days.

Poor bioavailability of pharmaceuticals presents a major challenge in designing oral dosage forms. The oral bioavailability depends on several factors, including aqueous solubility, drug permeability, dissolution rate, first-pass metabolism, presystemic metabolism, and susceptibility to efflux mechanisms. The most frequent causes of low oral bioavailability are attributed to poor solubility and low permeability. For orally administered drugs, solubility is the most important rate limiting parameter to achieve their desired concentration in systemic circulation for pharmacological response. Accordingly, liquid compositions containing active pharmaceutical ingredients that are completely solubilized in a liquid composition are more advantageous over suspension compositions. The extent of solubility of a substance in a specific solvent is measured as the saturation concentration, at which the addition of more solute does not increase its concentration in the solution. The extent of solubility ranges widely, from infinitely soluble (fully miscible) (for example, ethanol in water) to poorly soluble (for example, silver chloride in water). Solubility is based on the highest-dose strength of an immediate release product. A drug is considered highly soluble when the highest dose strength is soluble in 250 mL or less of aqueous media over the pH range of 1 to 7.5.

Accordingly, there remains a need for a highly bioavailable, highly soluble, stable valsartan oral solutions that can address these problems, while safely and effectively providing the proper and consistent administration of valsartan with accuracy and precision to patients who have difficulty swallowing solid dosage forms.

SUMMARY

Provided herein are stable oral liquid compositions including valsartan, as generally described herein. Also provided herein are methods including administering the stable oral liquid compositions herein to a subject.

One non-limiting aspect according to the present disclosure is directed to an oral liquid composition that comprises valsartan or a pharmaceutically acceptable salt or solvate thereof, a cyclodextrin and/or a cyclodextrin derivative, and at least one alkali salt. According to one non-limiting embodiment, the oral liquid composition comprises: about 12.0 mg/mL to about 80.0 mg/mL valsartan or a pharmaceutically acceptable salt or solvate thereof; about 1.0 mg/mL to about 80 mg/mL of a cyclodextrin or a cyclodextrin derivative; and an amount of at least one alkali salt sufficient to adjust the pH of the oral liquid composition to the range of about 5.5 to about 9.0.

A further non-limiting aspect according to the present disclosure is directed to an oral liquid composition comprising: about 60 mg/mL to about 68 mg/mL valsartan or a pharmaceutically acceptable salt or solvate thereof; about 1.0 mg/mL to about 100 mg/mL cyclodextrin and/or cyclodextrin derivative; and water. In various embodiments, the valsartan or pharmaceutically acceptable salt or solvate thereof is fully solubilized in the oral liquid composition. In certain non-limiting embodiments, the oral liquid composition comprises hydroxypropyl beta-cyclodextrin, e.g., about 25 mg/mL to about 75 mg/mL hydroxypropyl beta-cyclodextrin. In certain non-limiting embodiments, the oral liquid composition comprises beta-cyclodextrin, e.g., about 5 mg/mL to about 15 mg/mL beta-cyclodextrin. In certain non-limiting embodiments, the oral liquid composition comprises about 64 mg/mL valsartan, based on total volume of the composition.

A further non-limiting aspect according to the present disclosure is directed to an oral liquid composition comprising: about 28 mg/mL to about 36 mg/mL valsartan or a pharmaceutically acceptable salt or solvate thereof; about 1.0 mg/mL to about 100 mg/mL cyclodextrin and/or cyclodextrin derivative; and water. In various embodiments, the valsartan or pharmaceutically acceptable salt or solvate thereof is fully solubilized in the oral liquid composition. In certain non-limiting embodiments, the oral liquid composition comprises hydroxypropyl beta-cyclodextrin, e.g., about 25 mg/mL to about 75 mg/mL hydroxypropyl beta-cyclodextrin. In certain non-limiting embodiments, the oral liquid composition comprises beta-cyclodextrin, e.g., about 5 mg/mL to about 15 mg/mL beta-cyclodextrin. In certain non-limiting embodiments, the oral liquid composition comprises about 32 mg/mL valsartan, based on total volume of the composition.

A further non-limiting aspect of the present disclosure is directed to an oral liquid composition that comprises valsartan or a pharmaceutically acceptable salt or solvate thereof and polyethylene glycol. According to one non-limiting embodiment, the oral liquid composition comprises about 12.0 mg/mL to about 80.0 mg/mL valsartan and about 400 mg/mL to about 700 mg/mL of a polyethylene glycol.

A further non-limiting aspect of the present disclosure is directed to an oral liquid composition that comprises valsartan or a pharmaceutically acceptable salt or solvate thereof, polyethylene glycol, and propylene glycol. According to one non-limiting embodiment, the oral liquid composition comprises about 12.0 mg/mL to about 80.0 mg/mL valsartan or a pharmaceutically acceptable salt or solvate thereof, about 300 mg/mL to about 500 mg/mL of a polyethylene glycol, and 300 mg/mL to about 500 mg/mL propylene glycol.

A further non-limiting aspect according to the present disclosure is directed to a method of treatment comprising administering an oral liquid composition according to the present disclosure to a subject in need thereof. In certain non-limiting embodiments of the method, the oral liquid composition is administered to a subject to treat hypertension A further non-limiting aspect of the present disclosure is directed to a method of treatment comprising administering an oral liquid composition comprising valsartan or a pharmaceutically acceptable salt or solvate thereof, a cyclodextrin and/or a cyclodextrin derivative, and at least one alkali salt to a subject in need thereof. In certain non-limiting embodiments, the oral liquid composition comprises about 12.0 mg/mL to about 80.0 mg/mL valsartan or a pharmaceutically acceptable salt or solvate thereof, about 1.0 mg/mL to about 80 mg/mL of cyclodextrin and/or cyclodextrin derivative, and an amount of at least one alkali salt sufficient to adjust the pH of the oral liquid composition to the range of about 5.5 to about 9.0. In certain embodiments of the methods herein, the oral liquid composition is administered to a subject to treat hypertension.

A further non-limiting aspect of the present disclosure is directed to a method of treatment comprising administering an oral liquid composition comprising valsartan or a pharmaceutically acceptable salt or solvate thereof and polyethylene glycol to a subject in need thereof. In certain non-limiting embodiments, the oral liquid composition comprises about 12.0 mg/mL to about 80.0 mg/mL valsartan or a pharmaceutically acceptable salt or solvate thereof, and about 400 mg/mL to about 700 mg/mL of polyethylene glycol. In certain non-limiting embodiments of the methods herein, the oral liquid composition is administered to a subject to treat hypertension.

A further non-limiting aspect of the present disclosure is directed to an oral liquid composition that comprises about 12.0 mg/mL to about 80.0 mg/mL of valsartan or a pharmaceutically acceptable salt or solvate thereof, about 300 mg/mL to about 500 mg/mL of polyethylene glycol, and about 300 mg/mL to about 500 mg/mL of propylene glycol. In certain non-limiting embodiments of the methods herein, the oral liquid composition is administered to a subject to treat hypertension.

BRIEF DESCRIPTION OF THE DRAWINGS

Various features and characteristics of non-limiting and non-exhaustive embodiments disclosed and described in this specification may be better understood by reference to the accompanying figures, in which:

FIGS. 1A-C are views of a one non-limiting embodiment of a container that may be used to contain an oral liquid composition, as described herein, wherein FIG. 1A is an isometric view of the container, FIG. 1B is an elevational view of the container, and FIG. 1C is a plan view of a bottom of the container; and FIGS. 2A-2D are views of a non-limiting embodiment of a container closure that may be used in conjunction with the container shown in FIGS. 1A-1C, as described herein, wherein FIG. 2A is an isometric view of the container closure, FIG. 2B is an exterior top view of the container closure, FIG. 2C is an exterior elevational view of the container closure, and FIG. 2D is a sectional view of the container closure.

Figure 1A:

The reader will appreciate the foregoing details, as well as others, upon considering the following detailed description of various non-limiting and non-exhaustive embodiments according to the present disclosure.

DETAILED DESCRIPTION

Provided herein are embodiments of stable oral liquid compositions including valsartan or a pharmaceutically acceptable salt or solvate thereof. Such compositions can be useful in the treatment of hypertension, treatment of heart failure, and reduction of cardiovascular mortality in clinically stable patients with left ventricular failure or left ventricular dysfunction following myocardial infarction. The compositions can provide advantages over conventional oral solid dosage forms including valsartan, for example, ease of administration, improved absorption, increased patient compliance, and accurate/precise delivery of valsartan to the patient. Further, valsartan or the pharmaceutically acceptable salt or solvate thereof may be fully solubilized in the oral liquid compositions according to the present disclosure, providing oral liquid compositions having improved bioavailability relative to liquid compositions that are suspensions, in which valsartan is not fully solubilized.

As used herein, the terms "suspension" and "suspensions" refer to liquid formulations in which particles of a substance are suspended within a solvent and, thus, remain undissolved in the formulation. The degree to which a substance dissolves in a solvent to result in a solution is known as solubility. Solubility is the property of a solid, liquid, or gaseous chemical substance, referred to as the solute, to dissolve in a solid, liquid, or gaseous solvent. The solubility of a substance fundamentally depends on the physical and chemical properties of the solute and the solvent, as well as on temperature, pressure, and the presence of other chemicals (including those affecting pH) of the solution. As used herein, the phrase "fully solubilized" refers to the complete solubilization of a solute at a particular concentration in a solvent.

Certain segments of the population have difficulty ingesting and swallowing solid oral dosage forms. This often leads to non-compliance with the recommended therapy, which can result in less-than-effective therapy. Also, an increased risk of choking can occur when children or the elderly take solid dosage forms. Currently, a compounding pharmacist can prepare a liquid alternative to solid oral dosage forms including valsartan by crushing a solid dosage form including valsartan and mixing it into a liquid. However, forming valsartan liquid compositions using such a technique can have significant drawbacks, including, for example, forming suspensions rather than solutions, large variability in the actual dosage amount of valsartan in portions of the liquid composition, incomplete or inconsistent suspension of the solid dosage form in the liquid, rapid instability, and inconsistent formulation methods per compounding pharmacist.

It has now been discovered that an oral liquid composition that includes valsartan and a solubilizing agent surprisingly and unexpectedly provides markedly improved solubility of valsartan when the valsartan is present in relatively high concentrations (e.g., about 16 mg/mL, 32 mg/mL, or about 64 mg/mL). Further, it has been discovered that such compositions exhibit surprising and unexpected stability and, for example, certain embodiments of oral liquid compositions according to the present disclosure are stable for up to 12 months or more. It also has been observed that in certain embodiments, increasing pH of oral liquid compositions of the present disclosure to about 8.5 to about 9.0 further increases solubility of valsartan.

Embodiments of oral liquid compositions including valsartan or a pharmaceutically acceptable salt or solvate thereof according to the present disclosure provide safe and effective administration of valsartan for the treatment of hypertension, treatment of heart failure, and reduction of cardiovascular mortality in clinically stable patients with left ventricular failure or left ventricular dysfunction following myocardial infarction.

Various non-limiting embodiments of oral liquid compositions according to the present disclosure comprise valsartan or a pharmaceutically acceptable salt or solvate thereof, cyclodextrin (e.g., β-cyclodextrin or hydroxypropyl β-cyclodextrin), alkali salt (e.g., sodium hydroxide), and water. Alkali salt (i.e., basic salt) adjusts pH of the compositions to about 5.5 to about 9.0, improving solubility and stability of the valsartan at higher concentrations (e.g., about 16 mg/mL, 32 mg/mL, or about 64 mg/mL). It has been observed that combining the cyclodextrin and the alkali salt synergistically further enhances solubility and stability of valsartan in the oral liquid compositions.

Various non-limiting embodiments of oral liquid compositions according to the present disclosure comprise polyethylene glycol and/or propylene glycol which has been observed to improve solubility of valsartan in the compositions.

In some embodiments, the oral liquid compositions are substantially free of solids, whereby all components are fully solubilized. As used herein, the phrase "substantially free of solids" refers to the characteristic wherein a solution is essentially or fundamentally devoid of solid particulates.

In various non-limiting embodiments of oral liquid compositions according to the present disclosure, valsartan or a pharmaceutically acceptable salt or solvate thereof is present in a concentration ranging from about 12 mg/mL to about 46 mg/mL of the oral liquid composition, or at any value or in any range subsumed therein. In certain embodiments, valsartan or a pharmaceutically acceptable salt or solvate thereof is present in the oral liquid composition in a concentration ranging from about 12 mg/mL to about 44 mg/mL, about 12 mg/mL to about 42 mg/mL, about 13 mg/mL to about 40 mg/mL, about 14 mg/mL to about 38 mg/mL, about 15 mg/mL to about 36 mg/mL, about 16 mg/mL to about 32 mg/mL, about 18 mg/mL to about 30 mg/mL, about 18 mg/mL to about 28 mg/mL, about 18 mg/mL to about 26 mg/mL, about 18 mg/mL to about 24 mg/mL, about 18 mg/mL to about 22 mg/mL, about 18 mg/mL to about 20 mg/mL, about 26 mg/mL to about 38 mg/mL, about 20 mg/mL to about 44 mg/mL, about 20 mg/mL to about 42 mg/mL, about 20 mg/mL to about 40 mg/mL, about 20 mg/mL to about 38 mg/mL, about 20 mg/mL to about 36 mg/mL, about 20 mg/mL to about 34 mg/mL, about 22 mg/mL to about 44 mg/mL, about 25 mg/mL to about 44 mg/mL, about 28 mg/mL to about 44 mg/mL, about 30 mg/mL to about 44 mg/mL, about 22 mg/mL to about 40 mg/mL, about 24 mg/mL to about 38 mg/mL, about 26 mg/mL to about 37 mg/mL, about 28 mg/mL to about 36 mg/mL, about 29 mg/mL to about 37 mg/mL, or about 30 mg/mL to about 34 mg/mL, based on total volume of the oral liquid composition. In various embodiments, valsartan or a pharmaceutically acceptable salt or solvate thereof is present in a concentration of about 30 mg/mL, about 32 mg/mL, or about 34 mg/mL, based on total volume of the oral liquid composition.

In some embodiments, valsartan or a pharmaceutically acceptable salt or solvate thereof is present in a concentration ranging from about 45 mg/mL to about 80 mg/mL of the oral liquid composition, or at any value or in any range subsumed therein. In certain embodiments, valsartan or a pharmaceutically acceptable salt or solvate thereof is present in the oral liquid composition in a concentration ranging from about 45 mg/mL to about 78.0 mg/mL, about 45 mg/mL to about 75 mg/mL, about 45 mg/mL to about 73 mg/mL, about 46 mg/mL to about 72 mg/mL, about 48 mg/mL to about 70 mg/mL, about 50 mg/mL to about 69 mg/mL, about 55 mg/mL to about 68 mg/mL, about 58 mg/mL to about 67 mg/mL, about 59 mg/mL to about 66 mg/mL, about 60 mg/mL to about 65 mg/mL, about 62 mg/mL to about 66 mg/mL, about 48 mg/mL to about 80 mg/mL, about 50 mg/mL to about 80 mg/mL, about 55 mg/mL to about 80 mg/mL, about 58 mg/mL to about 80 mg/mL, about 60 mg/mL to about 80 mg/mL, about 64 mg/mL to about 80 mg/mL, or about 70 mg/mL to about 80 mg/mL, based on total volume of the oral liquid composition. In various embodiments, valsartan or a pharmaceutically acceptable salt or solvate thereof is present in a concentration of about 60 mg/mL, about 62 mg/mL, about 63 mg/mL, about 64 mg/mL, or about 68 mg/mL, based on total volume of the oral liquid composition.

Salts and solvates of valsartan are known in the literature and are typically more water soluble than free base. Non-limiting examples include crystalline or amorphous calcium/magnesium (or other alkali) salts of valsartan or hydrates thereof, for example, monohydrates, dihydrates, trihydrates, or pentahydrates. Solvates and hydrates of the salts may be present, for example, as mono-, di-, tri-, tetra-, penta-, hexa-solvates or hydrates, respectively. Examples of known salts of valsartan are provided in, for example, WO 02/06253 A1, entitled "Valsartan Salts", published Jan. 24, 2002, the entire disclosure of which is hereby incorporated herein by reference. WO'253 discloses, for example, salts of valsartan including the monosodium salt, the monopotassium salt, the dipotassium salt, the magnesium salt, the calcium salt, the bis-diethylammonium salt, the bis-dipropylammonium salt, the bis-dibutylammonium salt, the mono-L-arginine salt, the bis-L-arginine salt, the mono-L-lysine salt and the bis-L-lysine salt, as well as salt mixtures, or respectively, an amorphous form, a solvate, especially hydrate, as well as a polymorphous form thereof.

In some embodiments, oral liquid compositions according to the present disclosure further comprise cyclodextrin. As known to those having ordinary skill, cyclodextrins are a family of cyclic oligosaccharides, including of a macrocyclic ring of six to eight glucose subunits joined by α-1,4 glycosidic bonds, creating a generally cone-shaped molecule including a hydrophilic exterior and a hydrophobic interior. Cyclodextrins conventionally may be produced from starch by enzymatic conversion. Compounds within the family of cyclodextrins include a (alpha)-cyclodextrin (including six glucose subunits), β (beta)-cyclodextrin (seven glucose subunits), and γ (gamma)-cyclodextrin (eight glucose subunits). These core structures can be substituted with various groups and moieties to create particular cyclodextrin molecules. For example, the cyclodextrin structure's hydroxyl groups can be manipulated by chemical modification, with O-methylation and acetylation being typical conversions. In certain non-limiting embodiments, the oral liquid compositions according to the present disclosure include at least one of an alpha-cyclodextrin, a beta-cyclodextrin, or a gamma-cyclodextrin. For example, an oral liquid composition according to the present disclosure may include one or more of hydroxypropyl beta-cyclodextrin, sulfobutylether-beta-cyclodextrin, methyl-beta-cyclodextrin (MβCD), polymeric derivatives of β cyclodextrins such as polyethylene glycol-βCD (βCD-PEG), and dextran-βCD (βCD-dextran).

In certain non-limiting embodiments, cyclodextrin is present in oral liquid compositions according to the present disclosure in a concentration ranging from about 1.0 mg/mL to about 80 mg/mL of the oral liquid composition, or at any value or in any range subsumed therein, for example, in a concentration ranging from about 5.0 mg/mL to about 55 mg/mL based on total volume of the oral liquid composition. In certain embodiments, cyclodextrin is present in the oral liquid compositions in a concentration ranging from about 2 mg/mL to about 80 mg/mL, about 5 mg/mL to about 80 mg/mL, about 6 mg/mL to about 80 mg/mL, about 7 mg/mL to about 80 mg/mL, about 8 mg/mL to about 80 mg/mL, about 9 mg/mL to about 80 mg/mL, about 10 mg/mL to about 80 mg/mL, about 11 mg/mL to about 80 mg/mL, about 12 mg/mL to about 80 mg/mL, about 13 mg/mL to about 80 mg/mL, about 14 mg/mL to about 80 mg/mL, about 15 mg/mL to about 80 mg/mL, about 16 mg/mL to about 80 mg/mL, about 17 mg/mL to about 80 mg/mL, about 18 mg/mL to about 80 mg/mL, about 19 mg/mL to about 80 mg/mL, about 20 mg/mL to about 80 mg/mL, about 21 mg/mL to about 80 mg/mL, about 22 mg/mL to about 80 mg/mL, about 23 mg/mL to about 80 mg/mL, about 24 mg/mL to about 80 mg/mL, about 25 mg/mL to about 80 mg/mL, about 26 mg/mL to about 80 mg/mL, about 27 mg/mL to about 80 mg/mL, about 28 mg/mL to about 80 mg/mL, about 29 mg/mL to about 80 mg/mL, about 30 mg/mL to about 80 mg/mL, about 31 mg/mL to about 80 mg/mL, about 32 mg/mL to about 80 mg/mL, about 33 mg/mL to about 80 mg/mL, about 34 mg/mL to about 80 mg/mL, about 35 mg/mL to about 80 mg/mL, about 36 mg/mL to about 80 mg/mL, about 37 mg/mL to about 80 mg/mL, about 38 mg/mL to about 80 mg/mL, about 39 mg/mL to about 80 mg/mL, about 40 mg/mL to about 80 mg/mL, about 41 mg/mL to about 80 mg/mL, about 42 mg/mL to about 80 mg/mL, about 43 mg/mL to about 80 mg/mL, about 44 mg/mL to about 80 mg/mL, about 45 mg/mL to about 80 mg/mL, about 46 mg/mL to about 80 mg/mL, about 47 mg/mL to about 80 mg/mL, about 48 mg/mL to about 80 mg/mL, about 49 mg/mL to about 80 mg/mL, about 50 mg/mL to about 80 mg/mL, about 51 mg/mL to about 80 mg/mL, about 52 mg/mL to about 80 mg/mL, about 53 mg/mL to about 80 mg/mL, about 54 mg/mL to about 80 mg/mL, about 55 mg/mL to about 80 mg/mL, about 56 mg/mL to about 80 mg/mL, about 57 mg/mL to about 80 mg/mL, about 58 mg/mL to about 80 mg/mL, about 59 mg/mL to about 80 mg/mL, about 60 mg/mL to about 80 mg/mL, about 61 mg/mL to about 80 mg/mL, about 62 mg/mL to about 80 mg/mL, about 63 mg/mL to about 80 mg/mL, about 64 mg/mL to about 80 mg/mL, about 65 mg/mL to about 80 mg/mL, about 66 mg/mL to about 80 mg/mL, about 67 mg/mL to about 80 mg/mL, about 68 mg/mL to about 80 mg/mL, about 69 mg/mL to about 80 mg/mL, about 70 mg/mL to about 80 mg/mL, about 71 mg/mL to about 80 mg/mL, about 72 mg/mL to about 80 mg/mL, about 73 mg/mL to about 80 mg/mL, about 74 mg/mL to about 80 mg/mL, about 75 mg/mL to about 80 mg/mL, about 76 mg/mL to about 80 mg/mL, about 77 mg/mL to about 80 mg/mL, about 78 mg/mL to about 80 mg/mL, about 5 mg/mL to about 30 mg/mL, about 5 mg/mL to about 25 mg/mL, about 5 mg/mL to about 20 mg/mL, about 5 mg/mL to about 18 mg/mL, about 5 mg/mL to about 16 mg/mL, about 5 mg/mL to about 14 mg/mL, about 5 mg/mL to about 12 mg/mL, about 35 mg/mL to about 70 mg/mL, about 30 mg/mL to about 65 mg/mL, about 30 mg/mL to about 60 mg/mL, about 30 mg/mL to about 59 mg/mL, about 30 mg/mL to about 58 mg/mL, about 30 mg/mL to about 57 mg/mL, about 30 mg/mL to about 56 mg/mL, about 30 mg/mL to about 55 mg/mL, about 30 mg/mL to about 54 mg/mL, about 30 mg/mL to about 53 mg/mL, about 30 mg/mL to about 52 mg/mL, about 48 mg/mL to about 52 mg/mL, about 46 mg/mL to about 53 mg/mL, about 44 mg/mL to about 55 mg/mL, about 42 mg/mL to about 57 mg/mL, about 38 mg/mL to about 62 mg/mL, or about 36 mg/mL to about 64 mg/mL, based on total volume of the oral liquid composition. In various embodiments, the cyclodextrin is present in a concentration of about 8.0 mg/mL, about 10 mg/mL, about 12 mg/mL, about 48 mg/mL, about 50 mg/mL, or about 52 mg/mL, based on total volume of the oral liquid composition.

In certain non-limiting embodiments, the oral liquid compositions have a pH of about 5.5 to about 9.0, or any pH value or in any pH range subsumed therein. In various non-limiting embodiments, the oral liquid compositions have a pH of about 6.5 to about 8.5. In certain non-limiting embodiments, the oral liquid compositions have a pH ranging from about 5.9 to about 8.6, about 6.2 to about 7.8, about 6.5 to about 7.5, about 6.6 to about 7.4, about 6.7 to about 7.3, or about 6.9 to about 7.2. In various non-limiting embodiments, the oral liquid compositions have a pH of about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, or about 8.5.

Various non-limiting embodiments of oral liquid compositions according to the present disclosure comprise at least one alkali (basic) salt. In certain non-limiting embodiments, the alkali salt is or includes a group IA salt. In certain non-limiting embodiments, the alkali salt is or includes an alkali salt of sodium, calcium, or potassium. In certain embodiments, the alkali salt is or includes sodium hydroxide.

In some embodiments, alkali salt is present in the oral liquid composition in a concentration sufficient so that a pH of the oral liquid composition is about 5.5 to about 9.0, or is any pH value or within any pH range subsumed therein. In certain non-limiting embodiments, alkali salt is present in the oral liquid compositions in a concentration sufficient to provide a pH of about 5.9 to about 8.6, about 6.2 to about 7.8, about 6.5 to about 7.5, about 6.6 to about 7.4, about 6.7 to about 7.3, or about 6.9 to about 7.2. In various non-limiting embodiments, alkali salt is present in the oral liquid composition in a concentration sufficient to provide a pH of about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, or about 8.5.

In various non-limiting embodiments, the oral liquid compositions include alkali salt in a concentration sufficient to adjust the pH to a desired range disclosed herein. Certain embodiments of the oral liquid compositions include about 100 mg/mL to about 500 mg/mL of 1N NaOH, which may be introduced into the compositions in an amount sufficient to provide the desired concentration of NaOH in the oral liquid compositions.

In various non-limiting embodiments of oral liquid compositions according to the present disclosure, a solvent may be included in the oral liquid composition. The addition of one or more of the solvents to the oral liquid compositions may enhance solubility of valsartan in the liquid compositions. The solvent may include, for example, one or more of acetone, alcohol, ethyl alcohol, amylene hydrate, benzyl benzoate, butyl alcohol, canola oil, caprylocaproyl polyoxylglycerides, corn oil, cottonseed oil, diethylene glycol monoethyl ether, ethyl acetate, glycerin, hexylene glycol, isopropyl alcohol, lauroyl polyoxylglycerides, methyl alcohol, methylene chloride, methyl isobutyl ketone, mineral oil, oleoyl polyoxylglycerides, peanut oil, polyethylene glycol, polyethylene glycol monomethyl ether, propylene glycol, sesame oil, and stearoyl polyoxylglycerides.

In various non-limiting embodiments of oral liquid compositions according to the present disclosure, the compositions include polyethylene glycol and/or a polyethylene glycol derivative, for example, polyethylene glycol 400. Polyethylene glycol 400 is a polyethylene glycol having a molecular weight in the range of 380 to 420.

In various non-limiting embodiments, the present oral liquid compositions include about 150 mg/mL to about 900 mg/mL of polyethylene glycol, or any concentration or any concentration range subsumed therein. In certain embodiments, polyethylene glycol is present in a concentration ranging from about 150 mg/mL to about 750 mg/mL, about 200 mg/mL to about 700 mg/mL, about 250 mg/mL to about 650 mg/mL, about 250 mg/mL to about 600 mg/mL, about 250 mg/mL to about 550 mg/mL, about 250 mg/mL to about 500 mg/mL, about 250 mg/mL to about 450 mg/mL, about 250 mg/mL to about 400 mg/mL, about 250 mg/mL to about 350 mg/mL, about 450 mg/mL to about 750 mg/mL, about 500 mg/mL to about 700 mg/mL, about 400 mg/mL to about 800 mg/mL, about 400 mg/mL to about 750 mg/mL, about 400 mg/mL to about 730 mg/mL, about 400 mg/mL to about 700 mg/mL, about 400 mg/mL to about 680 mg/mL, about 400 mg/mL to about 650 mg/mL, about 400 mg/mL to about 630 mg/mL, about 400 mg/mL to about 600 mg/mL, about 450 mg/mL to about 800 mg/mL, about 480 mg/mL to about 800 mg/mL, about 500 mg/mL to about 800 mg/mL, about 530 mg/mL to about 800 mg/mL, about 550 mg/mL to about 800 mg/mL, about 560 mg/mL to about 800 mg/mL, about 570 mg/mL to about 800 mg/mL, about 450 mg/mL to about 750 mg/mL, about 480 mg/mL to about 730 mg/mL, about 500 mg/mL to about 720 mg/mL, about 550 mg/mL to about 680 mg/mL, about 560 mg/mL to about 650 mg/mL, about 570 mg/mL to about 630 mg/mL, about 575 to about 625 mg/mL, or about 600 mg/mL, based on the total volume of the oral liquid composition.

In some non-limiting embodiments, propylene glycol (propane-1,2-diol) and/or a propylene glycol derivative may be included in the oral liquid compositions according to the present disclosure. In some non-limiting embodiments, propylene glycol is present in the oral liquid compositions according to the present disclosure in a concentration ranging from about 200 mg/mL to about 700 mg/mL, based on the total volume of the oral liquid composition, or in any concentration or within any concentration range subsumed therein. In certain non-limiting embodiments, propylene glycol is present in a concentration ranging from about 300 mg/mL to about 400 mg/mL, about 200 mg/mL to about 500 mg/mL, about 250 mg/mL to about 480 mg/mL, about 250 mg/mL to about 450 mg/mL, about 250 mg/mL to about 430 mg/mL, about 250 mg/mL to about 400 mg/mL, about 250 mg/mL to about 380 mg/mL, about 250 mg/mL to about 370 mg/mL, about 220 mg/mL to about 500 mg/mL, about 270 mg/mL to about 500 mg/mL, about 280 mg/mL to about 500 mg/mL, about 290 mg/mL to about 500 mg/mL, about 300 mg/mL to about 500 mg/mL, about 310 mg/mL to about 500 mg/mL, about 320 mg/mL to about 500 mg/mL, about 270 mg/mL to about 480 mg/mL, about 290 mg/mL to about 460 mg/mL, about 310 mg/mL to about 420 mg/mL, about 330 mg/mL to about 370 mg/mL, about 300 mg/mL to 650 mg/mL, or about 350 mg/mL to about 600 mg/mL, based on total volume of the oral liquid composition. In various non-limiting embodiments, propylene glycol is present in a concentration of about 375 mg/mL to about 425 mg/mL, about 525 mg/mL to about 600 mg/mL, about 320 mg/mL, about 350 mg/mL, about 370 mg/mL, about 400 mg/mL, about 550 mg/mL, about 586 mg/mL, or about 600 mg/mL, based on total volume of the oral liquid composition.

In some non-limiting embodiments, a sorbate salt is present in the oral liquid composition according to the present disclosure. In some non-limiting embodiments of the oral liquid compositions according to the present disclosure including a sorbate salt, the sorbate salt is or includes a group IA or a group IIA sorbate salt. In various non-limiting embodiments, the sorbate salt is or includes one or more of lithium sorbate, potassium sorbate, sodium sorbate, calcium sorbate, or magnesium sorbate. In certain non-limiting embodiments, sorbate salt is present in a concentration sufficient to provide a stable composition, for example, providing anti-microbial activity that prevents growth and/or spread of bacteria and molds in the oral liquid composition. In various non-limiting embodiments, sorbate salt is present in a concentration of about 1 mg/mL to about 3 mg/mL, based on total volume of the oral liquid composition, or in any concentration or within any concentration range subsumed therein. In certain non-limiting embodiments, sorbate salt is present in the oral liquid composition in a concentration of about 0.8 mg/mL to about 3.2 mg/mL, about 0.9 mg/mL to about 3.1 mg/mL, about 1.1 mg/mL to about 2.9 mg/mL, about 1.2 mg/mL to about 2.8 mg/mL, about 1.3 mg/mL to about 2.7 mg/mL, about 1.4 mg/mL to about 2.6 mg/mL, about 1.5 mg/mL to about 2.5 mg/mL, about 1.5 mg/mL to about 2.4 mg/mL, about 1.6 mg/mL to about 2.3 mg/mL, about 1.7 mg/mL to about 2.3 mg/mL, about 1.8 mg/mL to about 2.2 mg/mL, about 1.9 mg/mL to about 2.1 mg/mL, about 1.6 mg/mL to about 2.2 mg/mL, or about 1.8 mg/mL to about 2.5 mg/mL, based on total volume of the oral liquid composition.

In some non-limiting embodiments including a sorbate salt, the sorbate salt in the oral liquid composition is or includes potassium sorbate. In certain non-limiting embodiments, potassium sorbate is present in a concentration of about 1.8 mg/mL to about 2.2 mg/mL, based on total volume of the oral liquid composition, or in any concentration or within any concentration range subsumed therein. In certain non-limiting embodiments, potassium sorbate is present in a concentration of about 0.8 mg/mL to about 3.2 mg/mL, about 0.9 mg/mL to about 3.1 mg/mL, about 1.1 mg/mL to about 2.9 mg/mL, about 1.2 mg/mL to about 2.8 mg/mL, about 1.3 mg/mL to about 2.7 mg/mL, about 1.4 mg/mL to about 2.6 mg/mL, about 1.5 mg/mL to about 2.5 mg/mL, about 1.5 mg/mL to about 2.4 mg/mL, about 1.6 mg/mL to about 2.3 mg/mL, about 1.7 mg/mL to about 2.3 mg/mL, about 1.8 mg/mL to about 2.2 mg/mL, about 1.9 mg/mL to about 2.1 mg/mL, about 1.6 mg/mL to about 2.2 mg/mL, or about 1.8 mg/mL to about 2.5 mg/mL, based on total volume of the oral liquid composition. In various non-limiting embodiments of the oral liquid composition, potassium sorbate is present in a concentration of about 1.8 mg/mL, about 1.9 mg/mL, about 2.0 mg/mL, about 2.1 mg/mL, or about 2.2 mg/mL, based on total volume of the oral liquid composition.

Various non-limiting embodiments of oral liquid compositions according to the present disclosure include paraben. In some non-limiting embodiments of the oral liquid composition, paraben present in the compositions is or includes one or more of methylparaben, ethylparaben, propylparaben, and/or butylparaben. In certain non-limiting embodiments, paraben is present in a concentration sufficient to provide a stable oral liquid composition, for example, providing antimicrobial activity that prevents growth and/or spread of bacteria and molds in the composition. In various non-limiting embodiments, paraben is present in a concentration of about 1 mg/mL to about 3 mg/mL, based on total volume of the oral liquid composition, or in any concentration or within any concentration range subsumed therein. In certain non-limiting embodiments, paraben is present in a concentration of about 0.5 mg/mL to about 4 mg/mL, about 0.6 mg/mL to about 3.9 mg/mL, about 0.7 mg/mL to about 3.8 mg/mL, about 0.8 mg/mL to about 3.7 mg/mL, about 0.9 mg/mL to about 3.6, about 1.1 mg/mL to about 2.9 mg/mL, about 1.2 mg/mL to about 2.8 mg/mL, about 1.3 mg/mL to about 2.7 mg/mL, about 1.4 mg/mL to about 2.6 mg/mL, or about 1.5 mg/mL to about 2.5 mg/mL, based on total volume of the oral liquid composition.

In some non-limiting embodiments of the oral liquid composition comprising paraben, the paraben is or includes methylparaben. In certain non-limiting embodiments, methylparaben is present in a concentration of from about 1.8 mg/mL to about 2.2 mg/mL, based on total volume of the oral liquid composition, or in any concentration or within any concentration range subsumed therein. In certain non-limiting embodiments, methylparaben is present in the oral liquid composition in a concentration of about 1.1 mg/mL to about 2.9 mg/mL, about 1.2 mg/mL to about 2.8 mg/mL, about 1.3 mg/mL to about 2.7 mg/mL, about 1.4 mg/mL to about 2.6 mg/mL, about 1.5 mg/mL to about 2.5 mg/mL, about 1.7 mg/mL to about 2.3 mg/mL, or about 1.9 mg/mL to about 2.1 mg/mL, based on total volume of the oral liquid composition. In various non-limiting embodiments, methylparaben is present in a concentration of about 1.8 mg/mL, about 1.9 mg/mL, about 2.0 mg/mL, about 2.1 mg/mL, or about 2.2 mg/mL, based on total volume of the oral liquid composition.

In various non-limiting embodiments, oral liquid compositions according to the present disclosure can comprise one or more additional excipients, including but not limited to, sweeteners, flavoring agents, stabilizers, coloring agents, thickeners, and the like. Additional excipients can be selected based on function and compatibility with the oral liquid compositions disclosed herein.

One or more sweeteners or sweetening agents can be used in the oral liquid compositions herein and can include any compounds that provide a sweet taste, including, for example, natural and synthetic sugars, natural and artificial sweeteners, natural extracts and any material that initiates a sweet sensation in a subject. Suitable sweeteners for inclusion in the oral liquid compositions include, but are not limited to, glucose, fructose, sucrose, xylitol, tagatose, sucralose, maltitol, isomaltulose, ISOMALT™ (hydrogenated isomaltulose), lactitol, sorbitol, mannitol, erythritol, trehalose, maltodextrin, polydextrose, and the like. Other sweeteners that may be included in the oral liquid compositions herein include, for example, glycerin, inulin, erythritol, maltol, acesulfame and salts thereof (e.g., acesulfame potassium), alitame, aspartame, neotame, sodium cyclamate, saccharin and salts thereof (e.g, saccharin sodium or saccharin calcium), neohesperidin dihydrochalcone, stevioside, thaumatin, and the like. Sweeteners can be used in the form of crude or refined products, such as, for example, hydrogenated starch hydrolysates, maltitol syrup, high fructose corn syrup, etc., and as branded products, e.g, SWEET AM™ liquid (Product Code 918.003 propylene glycol, ethyl alcohol, and proprietary artificial flavor combination, Flavors of North America), SWEET AM™ powder (Product Code 918.005—maltodextrin, sorbitol, and fructose combination and Product Code 918.010—water, propylene glycol, sorbitol, fructose, and proprietary natural and artificial flavor combination, Flavors of North America), PROSWEET™ sweetener (1-10% proprietary plant/vegetable extract and 90-99% dextrose combination, Virginia Dare), MALTISWEET™ sweetener (maltitol solution, Ingredion), SORBO™ sweetener (sorbitol and sorbitol/xylitol solution, SPI Polyols), INVERTOSE™ (high fructose corn syrup, Ingredion), and ORA-SWEET™ sugar-free flavored syrup (Paddock Laboratories, Inc.). Sweeteners can be used singly or in combinations of two or more. In some non-limiting embodiments including sweetener, the sweetener is or includes sucralose. Suitable concentrations of different sweeteners can be selected based on published information, manufacturers' data sheets, and/or by routine testing.

One or more flavoring agents can be used to enhance the taste or aroma of the oral liquid compositions herein. Suitable natural or synthetic flavoring agents can be selected from standard reference books, for example, Fenaroli's Handbook of Flavor Ingredients, 3rd edition (1995). Non-limiting examples of suitable natural flavors for inclusion in the oral liquid compositions, some of which can readily be simulated with synthetic agents or combinations thereof, include almond, anise, apple, apricot, bergamot, blackberry, blackcurrant, blueberry, cacao, caramel, cherry, cinnamon, clove, coffee, coriander, cranberry, cumin, dill, eucalyptus, fennel, fig, ginger, grape, grapefruit, guava, hop, lemon, licorice, lime, malt, mandarin, molasses, nutmeg, orange, peach, pear, peppermint, pineapple, raspberry, rose, spearmint, strawberry, tangerine, tea, tutti-frutti, vanilla, wintergreen, and the like. In certain non-limiting embodiments of the oral liquid compositions, flavoring agents include cherry, grape, and/or bubblegum flavoring agents.

Coloring agents can be included in non-limiting embodiments of the oral liquid compositions herein, for example, for identification and/or aesthetic purposes. Suitable coloring agents include, but are not limited to, FD&C Red No. 3, FD&C Red No. 20, FD&C Red No. 40, FD&C Yellow No. 6, FD&C Blue No. 2, D&C Green No. 5, D&C Orange No. 5, caramel, ferric oxide, or mixtures thereof.

The oral liquid compositions disclosed herein may be prepared in the forms of, for example and without limitation, aqueous solutions, nonaqueous solutions, juices, elixirs, and the like. Despite valsartan having low solubility, the oral liquid compositions herein surprisingly are solutions rather than suspensions, wherein no active ingredient is present as particulate matter or in a solid form in the compositions. Fully solubilizing the active ingredients, such as valsartan, in the oral liquid compositions herein provides advantages over their partially solubilized counterparts (e.g., suspensions, slurries, etc.). Such advantages include, for example, higher drug absorption and drug permeability, lending to improved bioavailability. However, low solubility active ingredients, such as valsartan, typically pose significant challenges to formulating liquid compositions in which the active ingredient is completely soluble and remains completely soluble until administration. The oral liquid compositions disclosed herein overcome those challenges.

Suitable liquid vehicles for use in non-limiting embodiments of the oral liquid compositions herein may be selected based on imparting desired qualities, including for example, clarity, nontoxicity, acceptable viscosity, compatibility with excipients, chemical inertness, palatability, acceptable odor and color, and economy. In some non-limiting embodiments, water is used as a vehicle in the oral liquid composition. In certain non-limiting embodiments, a syrup is used as a vehicle in the oral liquid composition. In various non-limiting embodiments, a juice is used as a vehicle in the oral liquid composition.

In some non-limiting embodiments of oral liquid compositions according to the present disclosure, the compositions are homogenous. As used herein, a "homogenous" liquid refers to a liquid that is uniform in appearance, identity, consistency, and drug concentration per volume. Non-homogenous liquids include such liquids that have, for example, varied coloring, and/or viscosity, as well as non-uniform drug concentration in each unit volume. Homogeneity in liquids can be assessed by qualitative identification or appearance tests and/or quantitative high performance liquid chromatography (HPLC) testing or the like. Exemplary qualitative testing includes visual inspection of the resultant liquid for air bubbles and/or undissolved solids which may cause variable dosing. Analytical HPLC testing can also determine drug concentration uniformity by examining aliquots of certain volume sections (e.g., 5 or 10 mL from the top, middle and bottom of a 150 mL bottle). The mixing methods and excipients disclosed herein are selected to impart a homogenous quality to the oral liquid compositions.

Mixing methods may include any type of mixing resulting in a homogenous oral liquid composition. Mixing can include one or more of stirring, shaking, swirling, agitating, or inverting. In some non-limiting embodiments, individual components of the oral liquid composition are added sequentially, concurrently, or in any combination thereof to a liquid vehicle. In some non-limiting embodiments, individual components are added sequentially, one at a time. In certain non-limiting embodiments, the sequential addition of individual components includes mixing for a certain time interval after each or some of the sequential additions. In various non-limiting embodiments, all individual components are added at the same time to a liquid vehicle and then mixed for a certain time interval. Various embodiments of the oral liquid compositions herein are stable under various storage conditions, including refrigerated and ambient conditions. As used herein, the term "stable" refers to a volume of the oral liquid composition retaining at least about 90%, at least about 95%, or at least about 98% of an initial amount of valsartan (or pharmaceutically acceptable salt or solvate thereof) after a given storage period under specified storage conditions. The term "stable" can also refer to an oral liquid composition including about 1% (w/w) or less total impurities or related substances, about 0.5% (w/w) or less total impurities or related substances, or about 0.4% (w/w) or less total impurities or related substances at the end of a given storage period under specified storage conditions. The term "stable" can also refer to an oral liquid composition having about 0.5% (w/w) or less individual impurities or related substances, or 0.2% (w/w) or less individual impurities or related substances at the end of a given storage period under specified storage conditions. The term "stable" can also refer to an oral liquid composition having less than about 102 total aerobic microbial count at the end of a given storage period under specified storage conditions. The term "stable" can also refer to an oral liquid composition having less than 101 total combined yeast and mold count at the end of a given storage period under specified storage conditions. The term "stable" can also refer to the absence or non-detection of *Escherichia coli* and/or *Burkholderia cepacia* within the oral liquid composition following a given storage period under specified storage conditions.

Methods of Treatment

Another aspect according to the present disclosure is directed to methods of treatment comprising administering an oral liquid composition according to the present disclosure to a subject in need thereof. In some embodiments, an oral liquid composition herein can be used to treat hypertension in a subject. Hypertension, as used herein, includes primary (essential) hypertension and/or secondary hypertension. Hypertension can be classified as cases in which blood pressure values are greater than or equal to 140/90 (systolic/diastolic) mm Hg in an adult subject. In certain embodiments, oral liquid compositions disclosed herein may be administered to treat primary (essential) hypertension in a subject. In other embodiments, oral liquid compositions disclosed herein may be administered to treat secondary hypertension in a subject. In certain embodiments, the subject is a pediatric subject. Pediatric hypertension can be classified as cases in which a child's blood pressure is greater than the 95th percentile for the patient's age, sex, and height. In certain non-limiting embodiments, the subject is a geriatric subject. Hypertension in geriatric patients is defined in a manner similar to that for adult patients, i.e., blood pressure values greater than or equal to 140/90 (systolic/diastolic) mm Hg.

In some non-limiting embodiments, oral liquid compositions herein can be used to treat heart failure. In certain non-limiting embodiments, the oral liquid compositions herein can be used to reduce cardiovascular mortality in clinically stable patients with left ventricular failure or left ventricular dysfunction following myocardial infarction.

Dosing

In one aspect, the oral liquid compositions herein are used for the treatment of diseases and conditions disclosed herein. In addition, a method for treating any of the diseases or conditions disclosed herein for a subject in need of such treatment involves administration of therapeutically effective amounts of the oral liquid compositions herein to the subject.

Dosages of the oral liquid compositions disclosed herein can be determined by any suitable method. Maximum tolerated dose (MTD) and maximum response dose (MRD) for valsartan can be determined via established animal and human experimental protocols. For example, toxicity and therapeutic efficacy of valsartan can be determined by standard pharmaceutical procedures in cell cultures or experimental animals, including, but not limited to, determination of the $LD_{50}$ (the dose lethal to 50% of the population) and the $ED_{50}$ (the dose therapeutically effective in 50% of the population). The dose ratio between the toxic and therapeutic effects is known as the therapeutic index, and it can be expressed as a ratio between $LD_{50}$ and $ED_{50}$. Valsartan dosages exhibiting high therapeutic indices are desirable. The data obtained from cell culture assays and animal studies can be used in formulating a range of dosage for use in humans. The dosage of such compounds lies preferably within a range of circulating concentrations that include the $ED_{50}$ with minimal toxicity. The dosage may vary within this range depending upon the dosage form employed and the route of administration utilized. Additional relative dosages, represented as a percent of maximal response or of maximum tolerated dose, are readily obtained via these protocols.

In some non-limiting embodiments, the dose of valsartan or a pharmaceutically acceptable salt or solvate thereof in a volume of the oral liquid composition herein for treating adult hypertension is about 80 mg or about 160 mg, administered once daily. In certain non-limiting embodiments, the amount of valsartan in a volume of an oral liquid composition herein administered once a day for treating adult hypertension is about 70 mg to about 170 mg, about 75 mg to about 165 mg, about 85 mg to about 155 mg, about 90 mg to about 150 mg, about 95 mg to about 140 mg, about 70 mg to about 330 mg, about 90 mg to about 300 mg, about 100 mg to about 280 mg, about 120 mg to about 250 mg, about 70 mg to about 325 mg, or about 85 mg to about 310 mg.

In other embodiments, the dose of valsartan in the oral liquid composition for treating heart failure in adult patients is about 40 mg twice daily. In yet other embodiments, valsartan in the oral liquid composition can be administered over a dose range of about 40 mg to about 160 mg twice daily for treating heart failure in adult patients. In certain embodiments, valsartan can be administered over a dose range of about 30 mg to about 170 mg, about 50 mg to about 150 mg, 70 mg to about 130 mg, 80 mg to about 120 mg, 90 mg to about 110 mg, or 45 mg to about 155 mg twice daily for treating heart failure in adult patients.

In other embodiments, the dose of valsartan in the oral liquid composition for reducing cardiovascular mortality in clinically stable adult patients with left ventricular failure or left ventricular dysfunction following myocardial infarction is about 20 mg twice daily. In other embodiments, valsartan in the oral liquid composition can be administered over a dose range of about 20 mg to about 160 mg twice daily for reducing cardiovascular mortality in clinically stable patients with left ventricular failure or left ventricular dysfunction following myocardial infarction. In certain embodiments, valsartan in the oral liquid composition can be administered over a dose range of about 10 mg to about 170 mg, about 35 mg to about 140 mg, about 50 mg to about 130 mg, about 60 mg to about 110 mg, about 70 mg to about 100 mg, about 25 mg to about 155 mg, or about 30 mg to about 145 mg, twice daily for reducing cardiovascular mortality in clinically stable patients with left ventricular failure or left ventricular dysfunction following myocardial infarction.

In some embodiments, the oral liquid composition is provided for administration to a human subject at a maximum tolerated dose (MTD) of valsartan. In certain embodiments, the amount of valsartan in the oral liquid composition administered to a human subject is from about 10% to about 90% of the MTD, from about 25% to about 75% of the MTD, or about 50% of the MTD. In certain embodiments, the amount of the oral liquid composition administered to a human subject ranges from about 20% to about 80% of the MTD, about 30% to about 70% of the MTD, about 40% to about 60% of the MTD, or about 20% to about 60% of the MTD. In certain other embodiments, the amount of the oral liquid composition administered is at least about 5%, 10%, 15%, 20%, 25%, 30%, 35%, 40%, 45%, 50%, 55%, 60%, 65%, 70%, 75%, 80%, 85%, 90%, 95%, 99%, or higher, or is within any range derivable therein, of the MTD for valsartan.

Administration

The oral liquid compositions described herein can be administered at a dosage disclosed herein or at other appropriate dose levels contemplated by a medical practitioner. In certain embodiments, the oral liquid compositions disclosed herein are administered for prophylactic and/or therapeutic treatments. In certain therapeutic applications, the oral liquid compositions are administered to a patient already suffering from an indication, e.g., hypertension, in a therapeutically effective amount sufficient to cure the disease or at least partially arrest or ameliorate the symptoms, e.g., lower blood pressure. Amounts effective for this use depend on, for example, the age of the patient, severity of the disease, previous therapy, the patient's health status, weight, and response to the oral liquid composition administered, and are within the judgment of the treating physician. Therapeutically effective amounts are optionally determined by methods including, but not limited to, a dose escalation clinical trial.

In certain embodiments wherein the patient's condition does not improve, upon the doctor's discretion, an oral liquid composition according to the present disclosure may be administered chronically, that is, for an extended period of time, including throughout the duration of the patient's life to ameliorate or otherwise control or limit the symptoms of the patient's disease. In some embodiments, administration of the oral liquid composition continues until complete or partial response of a disease occurs.

In some embodiments, an oral liquid composition herein is administered to a subject who is in a fasted state. In certain embodiments, an oral liquid composition herein is administered to a subject who is in a fed state.

Further Combinations

In some embodiments, the treatment of certain diseases or conditions (e.g., hypertension, heart failure, or reduction of cardiovascular mortality in clinically stable patients with left ventricular failure or left ventricular dysfunction following myocardial infarction) in a subject with the oral liquid compositions disclosed herein encompasses additional therapies and treatment regimens with other active pharmaceutical ingredients. In some embodiments, additional therapies and treatment regimens can include sequential or concurrent administration of a second active ingredient to a subject to treat the same disease or condition being treated with the oral liquid composition or a different disease or condition. In various embodiments, additional therapies and treatment regimens include sequential or concurrent administration of a second active ingredient to a subject to treat adjunct conditions associated with the disease or condition or a side effect from the oral liquid composition in the therapy.

Possible additional active ingredients for use in combination with an oral liquid composition as disclosed herein, include, but are not limited to, diuretics (loop, thiazide, potassium-sparing, and the like), beta blockers (metoprolol, propanolol, pronethalol, and the like), alpha blockers (phentolamine, phenoxybenzamine, tamsulosin, prazosin, and the like), mixed alpha and beta blockers (bucindolol, carvedilol, labetalol), calcium channel blockers (dilitazem, verapamil, dihydropyridines such as nifedipine, amlodipine, etc., and the like), angiotensin II receptor antagonists (saralasin, losartan, eprosartin, irbesartan, and the like), other ACE inhibitors (lisinopril, captopril, quinapril, ramipril, zofenopril, and the like), aldosterone antagonists (eplerenone, spironolactone and the like), vasodilators (hydralazine and the like), and alpha-2 agonists (clonidine, moxonidine, guanabenz, and the like).

EXAMPLES

Example 1. Preparation of Oral Liquid Compositions Including Valsartan

Eight oral liquid compositions were prepared including the ingredients listed in Table 1 (mg/mL concentrations) using methods described in Examples 2-7.

TABLE 1

Oral liquid compositions #1, #2, #3, #4, #5, #6, #7, and #8, including either 64 mg/mL valsartan or 32 mg/mL valsartan.

| Ingredient | #1 mg/mL | #2 mg/mL | #3 mg/mL | #4 mg/mL | #5 mg/mL | #6 mg/mL | #7 mg/mL | #8 mg/mL |
|---|---|---|---|---|---|---|---|---|
| Valsartan | 64 | 64 | 64 | 32 | 32 | 32 | 64 | 64 |
| Hydroxypropyl β-Cyclodextrin | 50 | — | — | 50 | — | — | — | — |
| β-Cyclodextrin | — | 10 | — | — | 10 | — | — | — |
| Sodium Hydroxide Solution (1N) | 300 | 300 | — | 150 | 300 | — | — | — |
| Polyethylene Glycol 400 | — | — | 586.1 | — | — | 300 | 350 | 250 |
| Propylene Glycol | — | — | — | — | — | 400 | 350 | 350 |
| Ethyl alcohol | — | — | — | — | — | — | 50 | — |
| Sorbitol Solution (70%) | — | — | — | — | — | — | — | 150 |
| Methylparaben | 2 | 2 | 2 | 2 | 2 | 2 | 2 | 2 |
| Potassium sorbate | 2 | 2 | 2 | 2 | 2 | 2 | 2 | 2 |
| Grape Flavor | 1 | 1 | 1 | 1 | 1 | 1 | 1 | 1 |
| Sucralose | 0.2 | 0.2 | 0.2 | 0.2 | 0.2 | 0.2 | 0.2 | 0.2 |
| Purified Water | 580.8 | 620.8 | 344.7 | 762.8 | 620.8 | 262.8 | 180.8 | 180.8 |

Example 2. Preparation of Oral Liquid Compositions #1 and #4

The following process describes the preparation of oral liquid compositions #1 and #4, having the ingredients listed in Table 1. Unless otherwise noted, all ingredients for oral liquid compositions #1 and #4 were added in the quantities/concentrations provided in Table 1, and the production steps were carried out at room temperature.

To prepare oral liquid compositions #1 and #4, hydroxypropyl β-cyclodextrin was mixed in purified water with constant stirring until there was no visible hydroxypropyl β-cyclodextrin particles in the mixture ("first mixture"). Methylparaben was added to the first mixture and stirred until there were no visible methylparaben particles, forming a second mixture. Potassium sorbate was added to the second mixture and stirred until there were no visible potassium sorbate particles, forming a third mixture. Valsartan was added to the third mixture and stirred until there were no visible valsartan particles, forming a fourth mixture. Sodium hydroxide solution (1N) was added to the fourth mixture to adjust the pH to a range of 7.5 to 8.5, forming a fifth mixture. Sucralose was added to the fifth mixture and stirred until all particles were dissolved, forming a final mixture. Flavoring was added to the final mixture, and then water was added quantum satis up to 1000 g. The pH of the final solution was measured and adjusted, if necessary, to a pH range of 7.5 to 8.5.

Example 3. Preparation of Oral Liquid Compositions #2 and #5

The following process describes the preparation of oral liquid compositions #2 and #5, having the ingredients listed in Table 1. Unless otherwise noted, all ingredients for the oral liquid compositions #2 and #5 were added in the quantities/concentrations provided in Table 1, and the production steps were carried out at room temperature.

To prepare oral liquid compositions #2 and #5, β-cyclodextrin was mixed in purified water with constant stirring until there was no visible β-cyclodextrin particles in the mixture ("first mixture"). Methylparaben was added to the first mixture and stirred until there were no visible methylparaben particles, forming a second mixture. Potassium sorbate was added to the second mixture and stirred until there were no visible potassium sorbate particles, forming a third mixture. Valsartan was added to the third mixture and stirred until there were no visible valsartan particles, forming a fourth mixture. Sodium hydroxide solution (1N) was added to the fourth mixture to adjust the pH to the range of 7.5 to 8.5, forming a fifth mixture. Sucralose was then added to the fifth mixture and stirred until all particles were dissolved, forming a final mixture. Flavoring was added to the final mixture, and then water was added quantum satis up to 1000 g. The pH of the final solution was measured and adjusted, if necessary, to a pH range of 7.5 to 8.5.

Example 4. Preparation of Oral Liquid Composition #3

The following process describes the preparation of oral liquid composition #3, the ingredients of which are listed in Table 1. Unless otherwise noted, all ingredients for the oral liquid composition #3 were added in the quantities/concentrations provided in Table 1, and the production steps were performed at room temperature.

To prepare oral liquid composition #3, valsartan was mixed in polyethylene glycol 400 with constant stirring until there was no visible valsartan particles in the mixture ("first mixture"). Methylparaben was added to the first mixture and stirred until there were no visible methylparaben particles, forming a second mixture. In a separate vessel, potassium sorbate was mixed in water until there were no visible potassium sorbate particles, forming a third mixture. Sucralose was then added to the third mixture and stirred until all particles were dissolved, forming a fourth mixture. Flavoring was added to the fourth mixture to create a fifth mixture. The fifth mixture (including potassium sorbate, water, sucralose, and flavoring) was slowly added to the second mixture (including valsartan, polyethylene glycol 400, and methylparaben) with stirring until the combined mixture was clear. Water was added to the combined mixture quantum satis up to 1000 g.

Example 5. Preparation of Oral Liquid Composition #6

The following process describes the preparation of oral liquid composition #6, the ingredients of which are listed in Table 1. Unless otherwise noted, all ingredients for the oral liquid composition #6 were added in the quantities/concentrations provided in Table 1, and the production steps were performed at room temperature.

To prepare oral liquid composition #6, valsartan was mixed in polyethylene glycol 400 with constant stirring until there was no visible valsartan particles in the mixture ("first mixture"). Propylene glycol was then added to the first mixture and stirred to create a second mixture. Methylparaben was added to the second mixture and stirred until there were no visible methylparaben particles, forming a third mixture. In a separate vessel, potassium sorbate was mixed in water until there were no visible potassium sorbate particles, forming a fourth mixture. Sucralose was then added to the fourth mixture and stirred until all particles were dissolved, forming a fifth mixture. Flavoring was added to the fifth mixture to create a sixth mixture. The sixth mixture (including potassium sorbate, water, sucralose, and flavoring) was slowly added to the third mixture (including valsartan, polyethylene glycol 400, propylene glycol, and methylparaben) with stirring until the combined mixture was clear. Water was added to the combined mixture quantum satis up to 1000 g.

Example 6. Preparation of Oral Liquid Composition #7

The following process describes the preparation of oral liquid composition #7, the ingredients of which are listed in Table 1. Unless otherwise noted, all components for the oral liquid composition #7 were added in the quantities/concentrations provided in Table 1, and all production steps were performed at room temperature.

To prepare oral liquid composition #7, valsartan was dissolved in ethanol and the solution was then mixed in polyethylene glycol 400 with constant stirring ("first mixture"). Propylene glycol was added to the first mixture and stirred to create a second mixture. Methylparaben was then added to the second mixture and stirred until there were no visible methylparaben particles, forming a third mixture. In a separate vessel, potassium sorbate was mixed in water until there were no visible potassium sorbate particles, forming a fourth mixture. Sucralose was then added to the fourth mixture and stirred until all particles were dissolved, forming fifth mixture. Flavoring was added to the fifth mixture to create a sixth mixture. The sixth mixture (including potassium sorbate, water, sucralose, and flavoring) was slowly added to the third mixture (including valsartan, polyethylene glycol 400, propylene glycol, and methylparaben) with stirring until the combined mixture ("final mixture") was clear. Water was added to the combined mixture quantum satis up to 1000 g. A precipitate formed in the final mixture one day later.

Example 7. Preparation of Oral Liquid Composition #8

The following process describes the preparation of oral liquid composition #8, the ingredients of which are listed in Table 1. Unless otherwise noted, all ingredients for the oral liquid composition #8 were added in the quantities/concentrations provided in Table 1, and the production steps were carried out at room temperature.

To prepare oral liquid composition #8, valsartan was mixed in polyethylene glycol 400 with constant stirring until there was no visible valsartan particles in the mixture ("first mixture"). Propylene glycol was then added to the first mixture and stirred to create a second mixture. Methylparaben was added to the second mixture and stirred until there were no visible methylparaben particles, forming a third mixture. 70% sorbitol solution (solution of 70% by weight sorbitol and 30% by weight water) was added to the third mixture. In a separate vessel, potassium sorbate was mixed in water until there were no visible potassium sorbate particles, forming a fourth mixture. Sucralose was added to the fourth mixture and stirred until all particles were dissolved, forming a fifth mixture. The sixth mixture (including potassium sorbate, water, and sucralose) was slowly added to the third mixture (including valsartan, polyethylene glycol 400, propylene glycol, methylparaben, and sorbitol) with stirring until the combined mixture was clear. Water and flavoring were added to the combined mixture quantum satis up to 1000 g.

Figure 1B:
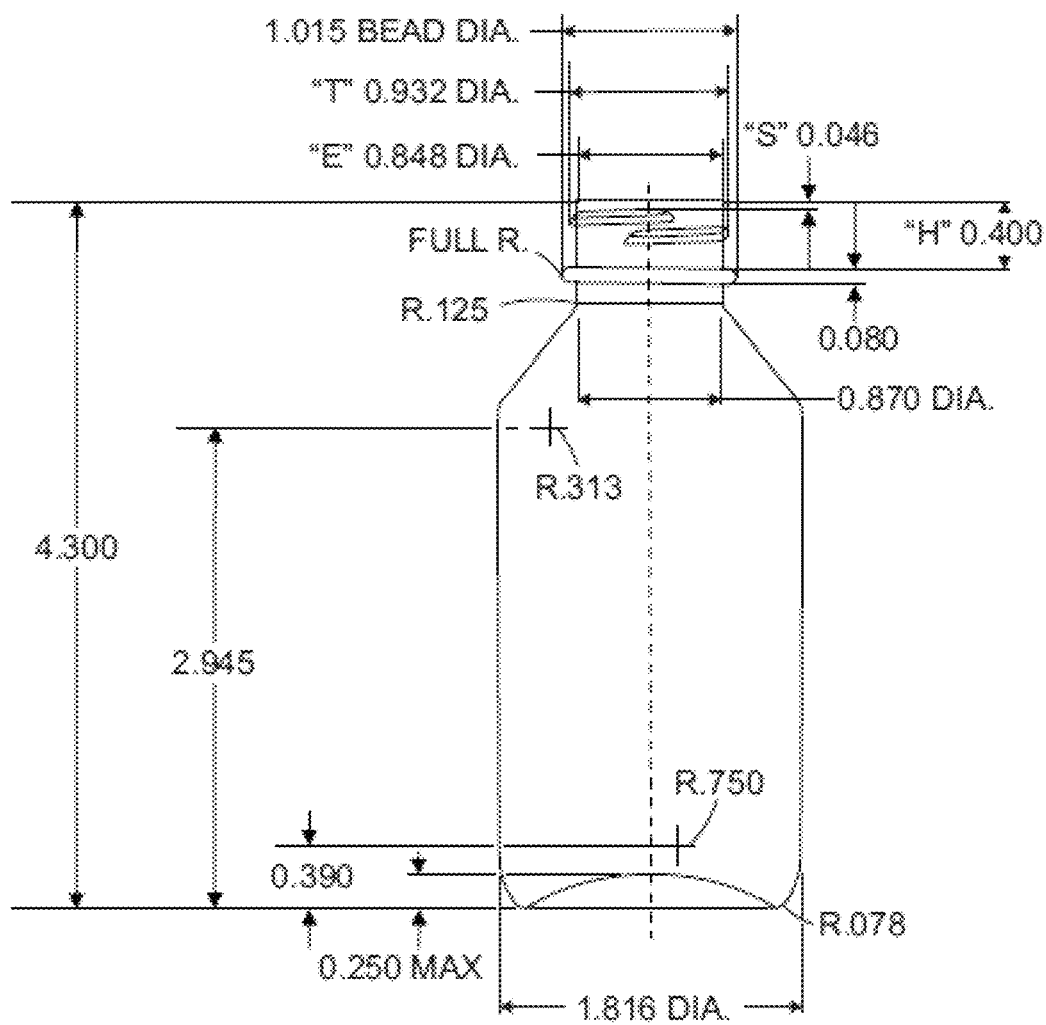
Figure 1C:
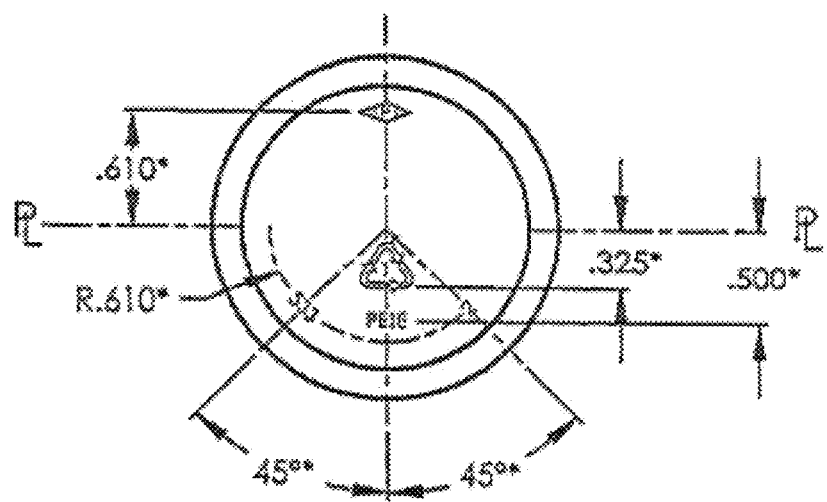
Figure 2A:
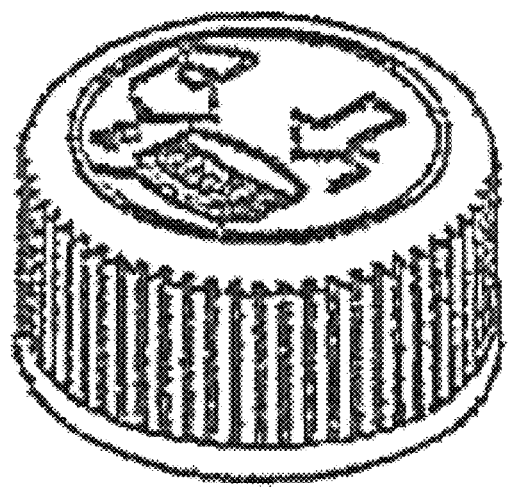
Figure 2B:
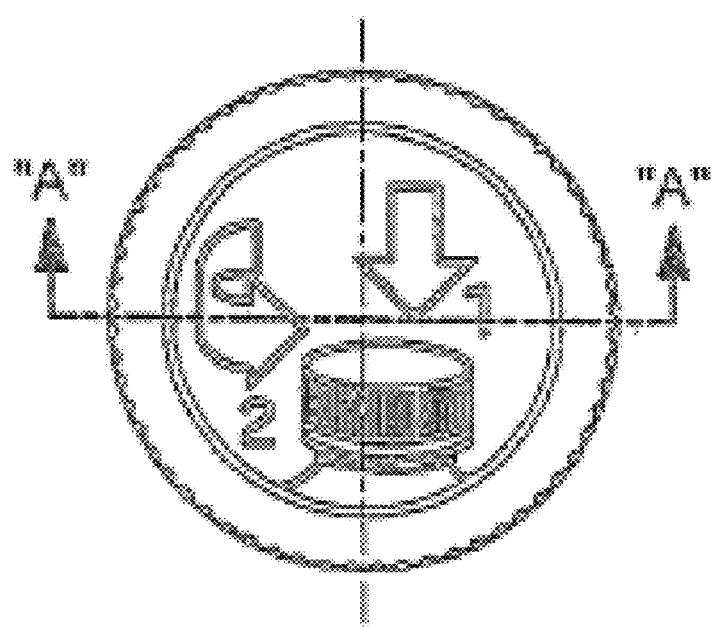
Figure 2C:
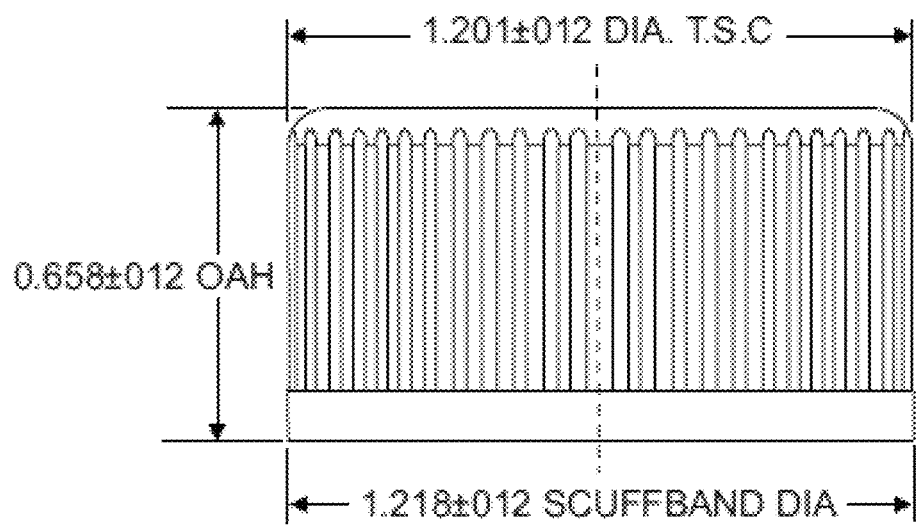
Figure 2D:
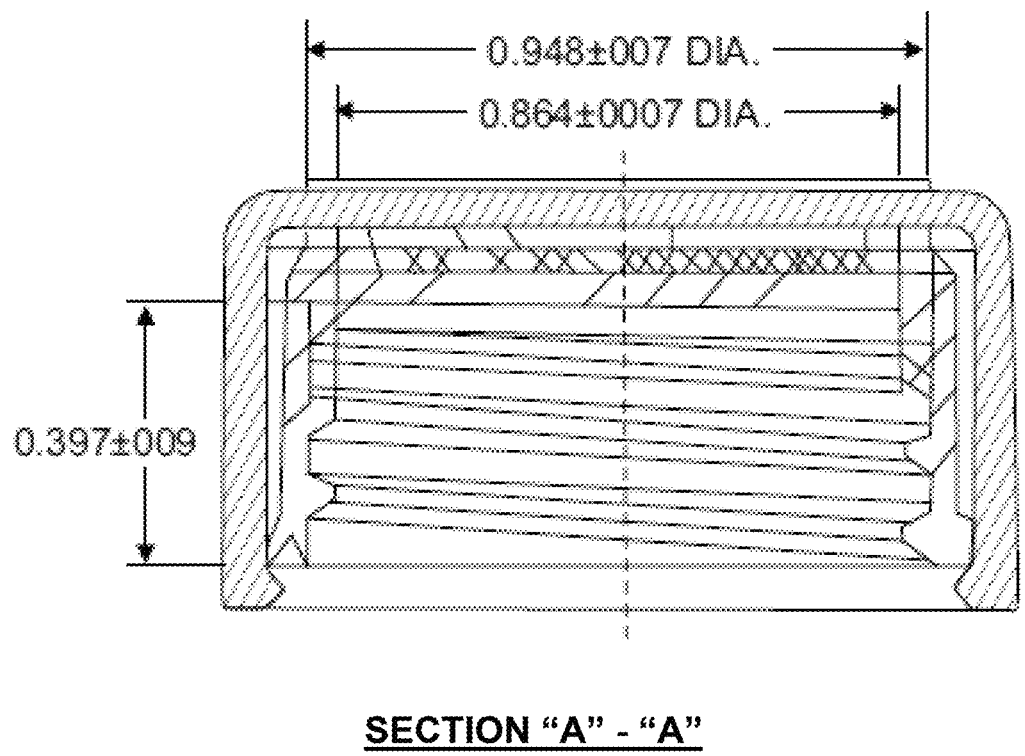

Example 8. Stability Study of the Oral Liquid Compositions Including Valsartan Stored in a Container Closure System For purposes of assessing stability, 120 mL samples of each of oral liquid compositions #1 to #6 made in Examples 1-5 were disposed separately in identical container closure systems. The container closure system included a four ounce (120 mL), boston round white (colorant: white 11078 AMPACET), high density polyethylene ("HDPE") (resin: MARLEX HHM 5502BN) bottle, shown in FIGS. 1A-1C. As shown in FIGS. 2A-2D, each container closure system also included a 24 mm SECURX™ ribbed side pictorial top (resin: INEOS H20E-00), white closure (colorant: white 11343 AMPACET), with a foam liner (liner: SELIG SEALING 0.035" C25 FSLE5-9). The samples were stored with the container closure system disposed upright in a calibrated stability chamber under one of the following storage conditions: standard or controlled room temperature conditions ("CRT") of 25° C.±2° C. and 60%±5% relative humidity (RH); intermediate conditions ("INT") of 30° C.±2° C. and 65% 5% RH; and accelerated conditions ("ACC") of 40° C.±2° C. and not more than (NMT) 75% RH.

Assay samples of the oral liquid compositions stored in the container closure system in the calibrated stability chamber were taken from the containers at set time intervals to assay for valsartan concentration. Samples were analyzed using a high performance liquid chromatography (HPLC) system equipped with a pump, autosampler, UV detector, and a suitable data acquisition system. The HPLC column used included packing L1 (C18), 5 m, 250 mm×4.6 mm. The HPLC parameters used included 230 nm detection, a flow rate of 1.5 mL/min, an injection volume of 20 μL, run at ambient temperature, for a run time of 25 minutes using a mobile phase of acetonitrile, DI water, and glacial acetic acid (40:60:0.1).

Table 2 reports the stability data for oral liquid compositions #1 through #6, stored under standard conditions (25° C.±2° C. and 60%±5% RH) in the sealed container closure system, for assay samples taken at 3, 6, 9, and 12 months.

TABLE 2

Stability results for oral liquid compositions #1 through #6 stored under standard conditions (25° C. ± 2° C. and 60% ± 5% RH) in container closure system.

| Compositions | Quantity of Valsartan | TEST | INITIAL | 3 MONTHS | 6 MONTHS | 9 MONTHS | 12 MONTHS |
|---|---|---|---|---|---|---|---|
| #1 | 64 mg/ml | Assay | 101.7* | 103.3* | 100.4* | 102.5* | 102.5* |
|  |  | pH | 7.4 | 7.3 | 7.1 | 7.3 | 7.2 |
| #2 | 64 mg/ml | Assay | 101.7* | 101.6* | 99.7* | 101.3* | 101.5* |
|  |  | pH | 8.2 | 8.1 | 8.1 | 7.8 | 7.7 |
| #3 | 64 mg/ml | Assay | 102.3* | 101.8* | 102.6* | 102.6* | 102.6* |
|  |  | pH | 4.6 | 4.7 | 4.6 | 4.2 | 4.5 |
| #4 | 32 mg/ml | Assay | 101.2* | 102.9* | 94.5* | 102.3* | 101.9* |
|  |  | pH | 8.2 | 8.0 | 8 | 7.6 | 7.7 |
| #5 | 32 mg/ml | Assay | 100.0* | 101.6* | 95.2* | 100.9* | 100.8* |
|  |  | pH | 8.0 | 7.9 | 7.8 | 7.6 | 7.5 |
| #6 | 32 mg/ml | Assay | 100.3* | 94.7* | 94.8* | 98.8* | 98* |
|  |  | pH | 4.8 | 4.5 | 4.7 | 4.3 | 4.7 |

*Assayed percent of Valsartan present at specified time

As shown by the results listed in Table 2, oral liquid compositions #1 through #6 were stable for at least 12 months when stored under standard conditions (25° C.±2° C. and 60% 5% RH) in the sealed container closure system. The stability assay showed that substantially greater than 90% of the original Valsartan was retained in oral liquid compositions #1 through #6 in the sealed container closure system stored under standard conditions for 12 months.

Table 3 reports stability data for oral liquid compositions #1 through #6, stored under intermediate conditions (30° C.±2° C. and 65%±5% RH) in the sealed container closure system, for assay samples taken at 3, 6, 9, and 12 months.

TABLE 3

Stability results for oral liquid compositions #1 to #6 stored under accelerated conditirons (40° C. ± 2° C. and NMT 75% RH) in container closure system.

| Compositions | Quantity of Valsartan | TEST | INITIAL | 3 MONTHS | 6 MONTHS | 9 MONTHS | 12 MONTHS |
|---|---|---|---|---|---|---|---|
| #1 | 64 mg/ml | Assay | 101.7* | 103.4* | 100.5* | 102.2* | 102.7* |
|  |  | pH | 7.4 | 7.3 | 7.0 | 7.2 | 7.2 |
| #2 | 64 mg/ml | Assay | 101.7* | 102.5* | 99.4* | 100.8* | 101.4* |
|  |  | pH | 8.2 | 8.0 | 8.0 | 7.6 | 7.5 |
| #3 | 64 mg/ml | Assay | 102.3* | 102.0* | 101.3* | 101.3* | 100.7* |
|  |  | pH | 4.6 | 4.6 | 4.5 | 4.2 | 4.5 |
| #4 | 32 mg/ml | Assay | 101.2* | 102.4* | 94.0* | 101.4* | 101.4* |
|  |  | pH | 8.2 | 8.0 | 8.1 | 7.5 | 7.6 |
| #5 | 32 mg/ml | Assay | 100.0* | 102.5* | 94.5* | 100.5* | 100.2* |
|  |  | pH | 8.0 | 7.8 | 7.9 | 7.4 | 7.3 |
| #6 | 32 mg/ml | Assay | 100.3* | 93.5* | 93.6* | 97.3* | 96.2* |
|  |  | pH | 4.8 | 4.5 | 4.5 | 4.2 | 4.6 |

*Assayed percent of Valsartan present at specified time

As indicated in Table 3, oral liquid compositions #1 through #6 of Examples 1-5 were stable for at least 12 months when stored under intermediate conditions (30° C.±2° C. and 65%±5% RH) in the sealed container closure system. The stability assay showed that substantially greater than 90% of the original valsartan was retained in oral liquid compositions #1 through #6 in the sealed container closure system stored under intermediate stability conditions for 12 months.

Table 4 reports stability data for oral liquid compositions #1 through #6 stored under accelerated conditions (40° C.±2° C. and NMT 75% RH) in the sealed container closure system, for assay samples taken at 1, 2, 3, and 6 months.

TABLE 4

Stability results for oral liquid compositions #1 to #6 stored under accelerated conditions (40° C. ± 2° C. and NMT 75% RH) in container closure system

| Compositions | Quantity of Valsartan | TEST | INITIAL | 3 MONTHS | 6 MONTHS | 9 MONTHS | 12 MONTHS |
|---|---|---|---|---|---|---|---|
| #1 | 64 mg/ml | Assay | 101.7* | 100.8* | 101.3* | 103.3* | 103* |
|  |  | pH | 7.4 | 7.2 | 7.1 | 7.2 | 7.2 |
| #2 | 64 mg/ml | Assay | 101.7* | 100.4* | 100.4* | 102.3* | 101.9* |
|  |  | pH | 8.2 | 7.9 | 7.7 | 7.6 | 8 |
| #3 | 64 mg/ml | Assay | 102.3* | 103.1* | 103.8* | 102.4* | 102* |
|  |  | pH | 4.6 | 4.1 | 4.5 | 4.5 | 4.5 |
| #4 | 32 mg/ml | Assay | 101.2* | 101.0* | 100.9* | 103.4* | 97.7* |
|  |  | pH | 8.2 | 7.9 | 7.8 | 7.8 | 8 |
| #5 | 32 mg/ml | Assay | 100.0* | 99.9* | 100.4* | 103.6* | 96.1* |
|  |  | pH | 8.0 | 7.6 | 7.5 | 7.4 | 7.7 |
| #6 | 32 mg/ml | Assay | 100.3* | 99.6* | 100.9* | 94.7* | 94.5* |
|  |  | pH | 4.8 | 4.1 | 4.6 | 4.6 | 4.8 |

*Assayed percent of Valsartan present at specified time

As indicated in Table 4, oral liquid compositions #1 through #6 of Examples 1-5 were stable for at least 6 months when stored under accelerated conditions (40° C.±2° C. and NMT 75% RH) in the sealed container closure system. The stability assay showed that substantially greater than 90% of the original Valsartan was retained in oral liquid compositions #1 through #6 in the sealed container closure system stored under accelerated conditions for 6 months.

The following numbered clauses are directed to various non-limiting examples of inventions according to the present disclosure:

1. An oral liquid composition comprising: about 60 mg/mL to about 68 mg/mL valsartan or a pharmaceutically acceptable salt or solvate thereof; about 1.0 mg/mL to about 100 mg/mL cyclodextrin; and water; provided that the valsartan or pharmaceutically acceptable salt or solvate thereof is fully solubilized in the oral liquid composition.

2. The oral liquid composition of clause 1, wherein the cyclodextrin comprises hydroxypropyl beta-cyclodextrin.

3. The oral liquid composition of clause 2, wherein the oral liquid composition comprises about 25 mg/mL to about 75 mg/mL hydroxypropyl beta-cyclodextrin.

4. The oral liquid composition of any of clauses 1-3, wherein the cyclodextrin comprises beta-cyclodextrin.

5. The oral liquid composition of any of clauses 1-4, wherein the oral liquid composition comprises about 5 mg/mL to about 15 mg/mL beta-cyclodextrin.

6. The oral liquid composition of any of clauses 1-5, wherein the oral liquid composition comprises about 64 mg/mL of the valsartan or pharmaceutically acceptable salt or solvate thereof.

7. The oral liquid composition of any of clauses 1-6, wherein a volume of the oral liquid composition retains at least about 95% of an initial amount of valsartan or pharmaceutically acceptable salt or solvate thereof when stored at a temperature ranging from about 38° C. to about 42° C. and a relative humidity not more than 75% for at least 3 months.

8. The oral liquid composition of any of clauses 1-6, wherein a volume of the oral liquid composition retains at least about 95% of an initial amount of valsartan or pharmaceutically acceptable salt or solvate thereof when stored at a temperature ranging from about 28° C. to about 32° C. and a relative humidity ranging from 60% to 70% for at least 6 months.

9. The oral liquid composition of any of clauses 1-6, wherein a volume of the oral liquid composition retains at least about 95% of an initial amount of valsartan or pharmaceutically acceptable salt or solvate thereof when stored at a temperature ranging from about 23° C. to about 27° C. and a relative humidity ranging from 55% to 65% for at least 9 months.

10. An oral liquid composition comprising: about 28 mg/mL to about 36 mg/mL valsartan or a pharmaceutically acceptable salt or solvate thereof, about 1.0 mg/mL to about 100 mg/mL cyclodextrin; and water; provided that the valsartan or pharmaceutically acceptable salt or solvate thereof is fully solubilized in the oral liquid solution.

11. The oral liquid composition of clause 10, wherein the cyclodextrin comprises hydroxypropyl beta-cyclodextrin.

12. The oral liquid composition of clause 11, wherein the oral liquid composition comprises about 25 mg/mL to about 75 mg/mL hydroxypropyl beta-cyclodextrin.

13. The oral liquid composition of any of clauses 10-12, wherein the cyclodextrin comprises beta-cyclodextrin.

14. The oral liquid composition of any of clauses 10-13, wherein the oral liquid composition comprises about 5 mg/mL to about 15 mg/mL beta-cyclodextrin.

15. The oral liquid composition of any of clauses 10-14, wherein the oral liquid composition comprises about 32 mg/mL valsartan or pharmaceutically acceptable salt or solvate thereof.

16. The oral liquid composition of any of clauses 10-15, wherein a volume of the oral liquid composition retains at least about 95% of an initial amount of valsartan or pharmaceutically acceptable salt or solvate thereof when stored at a temperature ranging from about 38° C. to about 42° C. and a relative humidity not more than 75% for at least 3 months.

17. The oral liquid composition of any of clauses 10-15, wherein a volume of the oral liquid composition retains at least about 95% of an initial amount of valsartan or pharmaceutically acceptable salt or solvate thereof when stored at a temperature ranging from about 28° C. to about 32° C. and a relative humidity ranging from 60% to 70% for at least 6 months.

18. The oral liquid composition of any of clauses 10-15, wherein a volume of the oral liquid composition retains at least about 95% of an initial amount of valsartan or pharmaceutically acceptable salt or solvate thereof when stored at a temperature ranging from about 23° C. to about 27° C. and a relative humidity ranging from 55% to 65% for at least 9 months.

19. An oral liquid composition comprising: about 60 mg/mL to about 68 mg/mL valsartan or a pharmaceutically acceptable salt or solvate thereof, about 400 mg/mL to about 700 mg/mL polyethylene glycol; and water; provided that the valsartan or pharmaceutically acceptable salt or solvate thereof is fully solubilized in the oral liquid composition.

20. The oral liquid composition of clause 19, wherein the polyethylene glycol comprises polyethylene glycol 400.

21. The oral liquid composition of any of clauses 19-20, wherein the oral liquid composition comprises about 64 mg/mL valsartan or pharmaceutically acceptable salt or solvate thereof.

22. The oral liquid composition of any of clauses 19-21, wherein a volume of the oral liquid composition retains at least about 95% of an initial amount of valsartan or pharmaceutically acceptable salt or solvate thereof when stored at a temperature ranging from about 38° C. to about 42° C. and a relative humidity not more than 75% for at least 3 months.

23. The oral liquid composition of any of clauses 19-21, wherein a volume of the oral liquid composition retains at least about 95% of an initial amount of valsartan or pharmaceutically acceptable salt or solvate thereof when stored at a temperature ranging from about 28° C. to about 32° C. and a relative humidity ranging from 60% to 70% for at least 6 months.

24. An oral liquid composition comprising: about 28 mg/mL to about 36 mg/mL valsartan or a pharmaceutically acceptable salt or solvate thereof, about 200 mg/mL to 400 mg/mL polyethylene glycol; 300 mg/to 500 mg/mL propylene glycol; and water; provided that the valsartan or pharmaceutically acceptable salt or solvate thereof is fully solubilized in the oral liquid composition.

25. The oral liquid composition of clause 24, wherein the polyethylene glycol comprises polyethylene glycol 400.

26. The oral liquid composition of any of clauses 24-25, wherein the oral liquid composition comprises about 32 mg/mL valsartan or pharmaceutically acceptable salt or solvate thereof.

27. The oral liquid composition of any of clauses 24-26, wherein a volume of the oral liquid composition retains at least about 95% of an initial amount of valsartan or pharmaceutically acceptable salt or solvate thereof when stored at a temperature ranging from about 38° C. to about 42° C. and a relative humidity not more than 75% for at least 2 months.

28. The oral liquid composition of any of clauses 24-26, wherein a volume of the oral liquid composition retains at least about 95% of an initial amount of valsartan or pharmaceutically acceptable salt or solvate thereof when stored at a temperature ranging from about 28° C. to about 32° C. and a relative humidity ranging from 60% to 70% for at least 9 months.

29. The oral liquid composition of any of clauses 24-26, wherein a volume of the oral liquid composition retains at least about 95% of an initial amount of valsartan or pharmaceutically acceptable salt or solvate thereof when stored at a temperature ranging from about 23° C. to about 27° C. and a relative humidity ranging from 55% to 65% for at least 9 months.

30. A method of treating hypertension comprising administering to a patient in need thereof the oral liquid composition of any of clauses 1-29.

It will be understood that the present description illustrates those aspects of the invention relevant to a clear understanding of the invention. Certain aspects that would be apparent to those of ordinary skill in the art and that, therefore, would not facilitate a better understanding of the invention have not been presented in order to simplify the present description. Although only a limited number of embodiments of the present invention are necessarily described herein, one of ordinary skill in the art will, upon considering the foregoing description, recognize that many modifications and variations of the invention may be employed. All such variations and modifications of the

What is claimed is:

1. An oral liquid composition consisting of:
   about 60 mg/mL to about 68 mg/mL valsartan or a pharmaceutically acceptable salt or solvate thereof;
   about 1.0 mg/mL to about 100 mg/mL cyclodextrin;
   alkali salt;
   optionally, sorbate salt;
   optionally, paraben;
   optionally, at least one sweetener selected from the group consisting of glucose, fructose, sucrose, tagatose, sucralose, trehalose, maltodextrin, polydextrose, inulin, maltol, acesulfame, alitame, aspartame, neotame, sodium cyclamate, saccharin, neohesperidin dihydrochalcone, stevioside, and thaumatin;
   optionally, at least one flavoring agent selected from the group consisting of almond, anise, apple, apricot, bergamot, blackberry, blackcurrant, blueberry, bubblegum, cacao, caramel, cherry, cinnamon, clove, coffee, coriander, cranberry, cumin, dill, eucalyptus, fennel, fig, ginger, grape, grapefruit, guava, hop, lemon, licorice, lime, malt, mandarin, molasses, nutmeg, orange, peach, pear, peppermint, pineapple, raspberry, rose, spearmint, strawberry, tangerine, tea, tutti-frutti, vanilla, and wintergreen; and
   water;
   provided that a pH of the oral liquid composition is 7.5 to 9.0 and the valsartan or pharmaceutically acceptable salt or solvate thereof is fully solubilized in the oral liquid composition.

2. The oral liquid composition of claim 1, wherein the cyclodextrin is hydroxypropyl beta-cyclodextrin.

3. The oral liquid composition of claim 2, wherein the cyclodextrin is hydroxypropyl beta-cyclodextrin in a concentration of about 25 mg/mL to about 75 mg/mL.

4. The oral liquid composition of claim 1, wherein the cyclodextrin is beta-cyclodextrin.

5. The oral liquid composition of claim 4, wherein the cyclodextrin is beta-cyclodextrin in a concentration of about 5 mg/mL to about 15 mg/mL.

6. The oral liquid composition of claim 3, wherein the valsartan or pharmaceutically acceptable salt or solvate thereof is in a concentration of about 64 mg/mL.

7. The oral liquid composition of claim 5, wherein the valsartan or pharmaceutically acceptable salt or solvate thereof is in a concentration of about 64 mg/mL.

8. The oral liquid composition of claim 1, provided that a volume of the oral liquid composition retains at least about 95% of an initial amount of valsartan or pharmaceutically acceptable salt or solvate thereof when stored at a temperature ranging from about 38° C. to about 42° C. and a relative humidity not more than 75% for at least 6 months.

9. An oral liquid composition consisting of:
   about 28 mg/mL to about 36 mg/mL valsartan or a pharmaceutically acceptable salt or solvate thereof;
   about 1.0 mg/mL to about 100 mg/mL cyclodextrin;
   alkali salt;
   optionally, sorbate salt;
   optionally, paraben;
   optionally, at least one sweetener selected from the group consisting of glucose, fructose, sucrose, tagatose, sucralose, trehalose, maltodextrin, polydextrose, inulin, maltol, acesulfame, alitame, aspartame, neotame, sodium cyclamate, saccharin, neohesperidin dihydrochalcone, stevioside, and thaumatin;
   optionally, at least one flavoring agent selected from the group consisting of almond, anise, apple, apricot, bergamot, blackberry, blackcurrant, blueberry, bubblegum, cacao, caramel, cherry, cinnamon, clove, coffee, coriander, cranberry, cumin, dill, eucalyptus, fennel, fig, ginger, grape, grapefruit, guava, hop, lemon, licorice, lime, malt, mandarin, molasses, nutmeg, orange, peach, pear, peppermint, pineapple, raspberry, rose, spearmint, strawberry, tangerine, tea, tutti-frutti, vanilla, and wintergreen; and
   water;
   provided that a pH of the oral liquid composition is 7.5 to 9.0 and the valsartan or pharmaceutically acceptable salt or solvate thereof is fully solubilized in the oral liquid composition.

10. The oral liquid composition of claim 9, wherein the cyclodextrin is hydroxypropyl beta-cyclodextrin.

11. The oral liquid composition of claim 10, wherein the cyclodextrin is hydroxypropyl beta-cyclodextrin in a concentration of about 25 mg/mL to about 75 mg/mL.

12. The oral liquid composition of claim 9, wherein the cyclodextrin is beta-cyclodextrin.

13. The oral liquid composition of claim 12, wherein the cyclodextrin is beta-cyclodextrin in a concentration of about 5 mg/mL to about 15 mg/mL.

14. The oral liquid composition of claim 11, wherein the valsartan or pharmaceutically acceptable salt or solvate thereof is in a concentration of about 32 mg/mL.

15. The oral liquid composition of claim 13, wherein the valsartan or pharmaceutically acceptable salt or solvate thereof is in a concentration of about 32 mg/mL.

16. The oral liquid composition of claim 9, provided that a volume of the oral liquid composition retains at least about 95% of an initial amount of valsartan or pharmaceutically acceptable salt or solvate thereof when stored at a temperature ranging from about 38° C. to about 42° C. and a relative humidity not more than 75% for at least 6 months.

17. A method of treating coronary artery disease comprising administering to a patient in need thereof an oral liquid composition consisting of:
   about 60 mg/mL to about 68 mg/mL valsartan or a pharmaceutically acceptable salt or solvate thereof;
   about 1.0 mg/mL to about 100 mg/mL cyclodextrin;
   alkali salt;
   optionally, sorbate salt;
   optionally, paraben;
   optionally, at least one sweetener selected from the group consisting of glucose, fructose, sucrose, tagatose, sucralose, trehalose, maltodextrin, polydextrose, inulin, maltol, acesulfame, alitame, aspartame, neotame, sodium cyclamate, saccharin, neohesperidin dihydrochalcone, stevioside, and thaumatin;
   optionally, at least one flavoring agent selected from the group consisting of almond, anise, apple, apricot, bergamot, blackberry, blackcurrant, blueberry, bubblegum, cacao, caramel, cherry, cinnamon, clove, coffee, coriander, cranberry, cumin, dill, eucalyptus, fennel, fig, ginger, grape, grapefruit, guava, hop, lemon, licorice, lime, malt, mandarin, molasses, nutmeg, orange, peach, pear, peppermint, pineapple, raspberry, rose, spearmint, strawberry, tangerine, tea, tutti-frutti, vanilla, and wintergreen; and
   water;
   provided that a pH of the oral liquid composition is 7.5 to 9.0 and the valsartan or pharmaceutically acceptable salt or solvate thereof is fully solubilized in the oral liquid composition.

18. The method of claim 17, wherein the cyclodextrin is hydroxypropyl beta-cyclodextrin in a concentration of about 25 mg/mL to about 75 mg/mL.

19. The method of claim 17, wherein the cyclodextrin is beta-cyclodextrin in a concentration of about 5 mg/mL to about 15 mg/mL.

20. The oral liquid composition of claim 1, wherein the pH of the oral liquid composition is 7.5 to 8.5.

21. The oral liquid composition of claim 1, wherein the pH of the oral liquid composition is 8.5 to 9.0.

22. The oral liquid composition of claim 1, provided that a volume of the oral liquid composition retains at least about 95% of an initial amount of valsartan or pharmaceutically acceptable salt or solvate thereof when stored at a temperature ranging from about 38° C. to about 42° C. and a relative humidity not more than 75% for at least 3 months.

23. The oral liquid composition of claim 9, wherein the pH of the oral liquid composition is 7.5 to 8.5.

24. The oral liquid composition of claim 9, wherein the pH of the oral liquid composition is 8.5 to 9.0.

25. The oral liquid composition of claim 9, provided that a volume of the oral liquid composition retains at least about 95% of an initial amount of valsartan or pharmaceutically acceptable salt or solvate thereof when stored at a temperature ranging from about 38° C. to about 42° C. and a relative humidity not more than 75% for at least 3 months.

26. The method of claim 17, wherein the pH of the oral liquid composition is 7.5 to 8.5.

27. The method of claim 17, wherein the pH of the oral liquid composition is 8.5 to 9.0.

28. The method of claim 17, provided that a volume of the oral liquid composition retains at least about 95% of an initial amount of valsartan or pharmaceutically acceptable salt or solvate thereof when stored at a temperature ranging from about 38° C. to about 42° C. and a relative humidity not more than 75% for at least 3 months.

29. The oral liquid composition of claim 1, wherein the alkali salt is sodium hydroxide.

30. The oral liquid composition of claim 9, wherein the alkali salt is sodium hydroxide.

31. The oral liquid composition of claim 17, wherein the alkali salt is sodium hydroxide.

32. The oral liquid composition of claim 1, wherein the paraben is one or more of methylparaben, ethylparaben, propylparaben, and butylparaben.

33. The oral liquid composition of claim 2, wherein the paraben is one or more of methylparaben, ethylparaben, propylparaben, and butylparaben.

34. The oral liquid composition of claim 1, consisting of:
    about 60 mg/mL to about 68 mg/mL valsartan or a pharmaceutically acceptable salt or solvate thereof;
    about 1.0 mg/mL to about 100 mg/mL cyclodextrin, wherein the cyclodextrin comprises hydroxypropyl beta-cyclodextrin;
    alkali salt;
    optionally, sorbate salt;
    optionally, one or more of methylparaben, ethylparaben, propylparaben, and butylparaben;
    optionally, at least one sweetener selected from the group consisting of glucose, fructose, sucrose, tagatose, sucralose, trehalose, maltodextrin, polydextrose, inulin, maltol, acesulfame, alitame, aspartame, neotame, sodium cyclamate, saccharin, neohesperidin dihydrochalcone, stevioside, and thaumatin;
    optionally, at least one flavoring agent selected from the group consisting of almond, anise, apple, apricot, bergamot, blackberry, blackcurrant, blueberry, bubblegum, cacao, caramel, cherry, cinnamon, clove, coffee, coriander, cranberry, cumin, dill, eucalyptus, fennel, fig, ginger, grape, grapefruit, guava, hop, lemon, licorice, lime, malt, mandarin, molasses, nutmeg, orange, peach, pear, peppermint, pineapple, raspberry, rose, spearmint, strawberry, tangerine, tea, tutti-frutti, vanilla, and wintergreen; and
    water;
    provided that a pH of the oral liquid composition is 7.5 to 9.0 and the valsartan or pharmaceutically acceptable salt or solvate thereof is fully solubilized in the oral liquid composition.

35. The oral liquid composition of claim 34, wherein the alkali salt is sodium hydroxide.

36. The oral liquid composition of claim 9, wherein the paraben is one or more of methylparaben, ethylparaben, propylparaben, and butylparaben.

37. The oral liquid composition of claim 10, wherein the paraben is one or more of methylparaben, ethylparaben, propylparaben, and butylparaben.

38. The oral liquid composition of claim 9, consisting of:
    about 28 mg/mL to about 36 mg/mL valsartan or a pharmaceutically acceptable salt or solvate thereof;
    about 1.0 mg/mL to about 100 mg/mL cyclodextrin, wherein the cyclodextrin comprises hydroxypropyl beta-cyclodextrin;
    alkali salt;
    optionally, sorbate salt;
    optionally, one or more of methylparaben, ethylparaben, propylparaben, and butylparaben;
    optionally, at least one sweetener selected from the group consisting of glucose, fructose, sucrose, tagatose, sucralose, trehalose, maltodextrin, polydextrose, inulin, maltol, acesulfame, alitame, aspartame, neotame, sodium cyclamate, saccharin, neohesperidin dihydrochalcone, stevioside, and thaumatin;
    optionally, at least one flavoring agent selected from the group consisting of almond, anise, apple, apricot, bergamot, blackberry, blackcurrant, blueberry, bubblegum, cacao, caramel, cherry, cinnamon, clove, coffee, coriander, cranberry, cumin, dill, eucalyptus, fennel, fig, ginger, grape, grapefruit, guava, hop, lemon, licorice, lime, malt, mandarin, molasses, nutmeg, orange, peach, pear, peppermint, pineapple, raspberry, rose, spearmint, strawberry, tangerine, tea, tutti-frutti, vanilla, and wintergreen; and
    water;
    provided that a pH of the oral liquid composition is 7.5 to 9.0 and the valsartan or pharmaceutically acceptable salt or solvate thereof is fully solubilized in the oral liquid composition.

39. The oral liquid composition of claim 38, wherein the alkali salt is sodium hydroxide.

40. The method of claim 17, wherein the paraben is one or more of methylparaben, ethylparaben, propylparaben, and butylparaben.

41. The method of claim 17, wherein the oral liquid composition consists of:
    about 60 mg/mL to about 68 mg/mL valsartan or a pharmaceutically acceptable salt or solvate thereof;
    about 1.0 mg/mL to about 100 mg/mL cyclodextrin, wherein the cyclodextrin comprises hydroxypropyl beta-cyclodextrin;
    alkali salt;
    optionally, sorbate salt;
    optionally, one or more of methylparaben, ethylparaben, propylparaben, and butylparaben;

optionally, at least one sweetener selected from the group consisting of glucose, fructose, sucrose, tagatose, sucralose, trehalose, maltodextrin, polydextrose, inulin, maltol, acesulfame, alitame, aspartame, neotame, sodium cyclamate, saccharin, neohesperidin dihydrochalcone, stevioside, and thaumatin;

optionally, at least one flavoring agent selected from the group consisting of almond, anise, apple, apricot, bergamot, blackberry, blackcurrant, blueberry, bubblegum, cacao, caramel, cherry, cinnamon, clove, coffee, coriander, cranberry, cumin, dill, eucalyptus, fennel, fig, ginger, grape, grapefruit, guava, hop, lemon, licorice, lime, malt, mandarin, molasses, nutmeg, orange, peach, pear, peppermint, pineapple, raspberry, rose, spearmint, strawberry, tangerine, tea, tutti-frutti, vanilla, and wintergreen; and water;

provided that a pH of the oral liquid composition is 7.5 to 9.0 and the valsartan or pharmaceutically acceptable salt or solvate thereof is fully solubilized in the oral liquid composition.

42. The method of claim 41, wherein the alkali salt is sodium hydroxide.

\* \* \* \* \*